(12) United States Patent
Dedera et al.

(10) Patent No.: US 7,378,253 B2
(45) Date of Patent: May 27, 2008

(54) METHODS OF THERAPY AND DIAGNOSIS USING IMMUNOTARGETING OF CD84HY1-EXPRESSING CELLS

(75) Inventors: Douglas Dedera, Castro Valley, CA (US); Jian Rui Wang, San Jose, CA (US); Peter Emtage, Edmonton (CA)

(73) Assignee: Novelo, Inc., San Carlos, CA (US)

(*) Notice: Subject to any disclaimer, the term of this patent is extended or adjusted under 35 U.S.C. 154(b) by 166 days.

(21) Appl. No.: 11/330,768

(22) Filed: Jan. 11, 2006

(65) Prior Publication Data
US 2006/0104977 A1 May 18, 2006

Related U.S. Application Data

(63) Continuation of application No. 10/327,413, filed on Dec. 19, 2002, now Pat. No. 7,029,677, which is a continuation-in-part of application No. 10/078,080, filed on Feb. 15, 2002, now abandoned, which is a continuation-in-part of application No. PCT/US01/02613, filed on Jan. 25, 2001, which is a continuation-in-part of application No. 09/645,476, filed on Aug. 24, 2000, now abandoned, which is a continuation-in-part of application No. 09/491,404, filed on Jan. 25, 2000, now abandoned.

(51) Int. Cl.
*G01N 33/53* (2006.01)

(52) U.S. Cl. ............... 435/7.23; 435/7.1; 435/7.21

(58) Field of Classification Search .............. None
See application file for complete search history.

(56) References Cited

FOREIGN PATENT DOCUMENTS

WO   WO 01/79454   10/2001

OTHER PUBLICATIONS

Behr et al., Experimental studies on the role of antibody fragments in cancer radio-immunotherapy: Influence of radiation dose and dose rate on toxicity and anti-tumor efficacy, *Int. J. Cancer* 77:787-795 (1998).
Bottino et al., NTB-A, a novel SH2D1A-associated surface molecule contributing to the inability of natural killer cells to kill Epstein-Barr virus-infected B cells in X-linked lymphoproliferative disease, *J. Exp. Med.* 194:235-246 (2001).
de la Fuente et al., CD84 leukocyte antigen is a new member of the Ig superfamily, *Blood* 90:2398-2405 (1997).
Hornick et al., "Chimeric CLL-1 antibody fusion proteins containing granulocyte-macrophage colony-stimulating factor or Interleukin-2 with specificity for B-cell malignancies exhibit enhanced effector functions while retaining tumor targeting properties," *Blood* 89:4437-4447 (1997).
Jiang and Moller, "In Vitro effects $HgCl_2$ on murine lymphocytes. I. Preferable activation of CD4+ T cells in a responder strain," *J. Immunol.* 154:3138-3146 (1995).
Martin et al., "CD84 functions as a homophilic adhesion molecule and enhances IFN-γsecretion: Adhesion is mediated by Ig-like domain 1," *J. Immunol.* 167:3668-3676 (2001).
Ozaki, et al., "Immunotherapy of Multiple Myeloma With A Monoclonal Antibody Directed Against a Plasma Cell-Specific Antigen, HM1.24," *Blood* 90:3179-3186 (1997).
Racila et al., Detection and characterization of carcinoma cells in the blood, *Proc. Natl. Acad. Sci. USA* 95:4589-4594 (1998).
Simpson et al., "Retinal VEGF mRNA measured by SYBR Green I fluorescence: A versatile approach to quantitative PCR," *Molec, Vision* 6:178-183 (2000).
Yang et al., "Potent suppression of the adaptive immune response in mice upon dietary exposure to the potent peroxisome proliferators, perfluorooctanoic acid," *Int. Immunopharm.* 2:389-397 (2002).
"Approved Biotechnology Drugs," Biotechnology Industry Drugs, printed Jan. 19, 2005.
Davis et al., "Rituximab anti-CD20 monoclonal antibody therapy in non-Hodgkin's lymphoma: safety and efficacy of re-treatment," *J. Clin. Oncol.* 18:3135-3143 (2000).
Maloney et al., "IDEC-C2B8 (Rituximab) anti-CD20 monoclonal antibody therapy in patients with relapsed low-grade non-Hodgkin's lymphoma," Blood 90:2188-2195 (1997).
Burk and Matuszewski, "Muromonab-CD3 and antithymocyte globulin in renal transplantation," Ann. Pharmacother. 31:1370-1377 (1997).
White et al., "Antibody-targeted immunotherapy for treatment of malignancy," Ann. Rev. Med. 52:125-145 (2001).
Wilde and Goa, "Muromonab CD3: A reappraisal of its pharmacology and use as prophylaxis of solid organ transplant rejection," Drugs 51:865-894 (1996).
Fundamental Immunology, 4th edition, ed. William Paul, pp. 58-59, 91-94, and 106-108 (1998).
Harris and Emery, "Therapeutic antibodies—the coming of age," TIBTECH 11:42-44 (1993).
Waldmann, "Monoclonal antibodies in diagnosis and therapy," Science 252:1657-1662 (1991).
Dillman, "Antibodies as cytotoxic therapy," *J. Clin. Oncol.* 12:1497-1515 (1994).

*Primary Examiner*—Sheela J. Huff
(74) *Attorney, Agent, or Firm*—Renée S. Polizotto

(57) ABSTRACT

Certain cells, including types of cancer cells such as lymphomas, are capable of expressing high levels of CD84Hy1. Immunotargeting using CD84Hy1 polypeptides, nucleic acids encoding for CD84Hy1 polypeptides and anti-CD84Hy1 antibodies provides a method of killing or inhibiting that growth of CD84HY1Protein-expressing cancer cells. Methods of immunotherapy and diagnosis of disorders associated with CD84Hy1 protein-expressing cells are described.

4 Claims, 1 Drawing Sheet

FIG. 1

```
ATG TTG TGG CTG TTC CAA TCG CTC CTG TTT GTC TTC TGC TTT GGC CCA GGG AAT GTA GTT
 M   L   W   L   F   Q   S   L   L   F   V   F   C   F   G   P   G   N   V   V
TCA CAA AGC TTA ACC CCA TTG ATG AAG GAG AAC GGG ATT CTG ACT TTC AAT GTA ACT CTT
 S   Q   S   L   T   P   L   M   K   E   N   G   I   L   T   F   N   V   T   L
CCC CTG GAG TTT CCT GCA GGA CCC CAT TTC ATC AAC TTC CCA GAA ATC TGG CTT GAA ACA
 P   L   E   F   P   A   G   P   H   F   I   N   F   P   E   I   W   L   E   T
TCT CTT GCC TTC ATA GTA CTG AAC TTC ACA CAG TCC TAC AAA AGT CCA GAA ATC CAC GTG ACT AAT CCG
 S   L   A   F   I   V   L   N   F   T   Q   S   Y   K   S   P   E   I   H   V   T   N   P
AAA CAG GGA AAG CGA CTG AAC TTC CAA CAG TCC TTG CAA ACC TTG CAA CTC AGC AAC CTG AAG
 K   Q   G   K   R   L   N   F   Q   Q   S   L   Q   T   L   Q   L   S   N   L   K
ATA GAA GAC ACA GGC TCT TAC AGA GCC CAA CTG AGG ATA TCC GCA AAG CAC AGT CTG TCC
 I   E   D   T   G   S   Y   R   A   Q   L   R   I   S   A   K   H   S   L   S
AGT TAC ACT CTG AGG ATA TTA AGA CAA CTG CTC CAT GTT ACC AAT CAC AGT CAG
 S   Y   T   L   R   I   L   R   Q   L   L   H   V   T   N   H   S   Q
CTA TTT CAG AAT ATG ACC TGT GAG CTC CAT CTG GGA AAC ACA ATA CAG TGC TCT TCA GAT GCA GAT GAC
 L   F   Q   N   M   T   C   E   L   H   L   G   N   T   I   Q   C   S   S   D   A   D   D
AAT GTC TCA TTC AGA TGG GAG GCC ATT TCC AGT CTT ACC ACC CAG AAG CAG CCA ATC CTC ACT
 N   V   S   F   R   W   E   A   I   S   S   L   T   T   Q   K   Q   P   I   L   T
GTC TCC TGG GAC CCC CCG GAT ATT TCC TCT GTC TCT GCC TCT AGT CAG GTT TCT GGG ATA GCA GAG AAT GCT
 V   S   W   D   P   P   D   I   S   S   V   S   A   S   S   Q   V   S   G   I   A   E   N   A
GTC AGT AAT TTA ACA ATC TTT ATG CTG TTT AGG AGA AGA CTA GAG ATA TGC CTA ATC CAA
 V   S   N   L   T   I   F   M   L   F   R   R   R   L   E   I   C   L   I   Q
TAT ACA GAT ACC AAA ATG CTG CTT TTA TTG GTT TTG AGG AAA AGA AAC CTA CGA AGG CTA GTT TCT GGT TTC
 Y   T   D   T   K   M   L   L   L   V   L   R   K   R   N   L   R   R   L   V   S   G   F
ATC ATA CTG GAC TTA CTT TTG GTT TCC GAG TCC GCA AGG AAC CTA AAC TCT TGT TCT ACT CAG
 I   I   L   D   L   L   L   V   S   E   S   A   R   N   L   N   S   C   S   T   Q
CGA ACA CAG GGC TAT GCT CAG GTC ACT CAT CGC CAA GTC GAA AAC TCA AAC ACG AAC
 R   T   Q   G   Y   A   Q   V   T   H   R   Q   V   E   N   S   P   T   N
AAC ACT GTG TAT ACT ATC ACA ATT TAC TCC ACA ATT AAT CAT CAT TGG GAA GAG ACA CCT AGA
 N   T   V   Y   T   I   T   I   Y   S   T   I   N   H   H   W   E   E   T   P   R
GAA AAT GAT ACT ACA ATT TAC CCA GTC CCA ATT CCC AAG AGT AGT CCC AAA ACT
 E   N   D   T   T   I   Y   S   T   I   N   H   S   K   E   S   K   P   T
TCT TCC AGG GCA ACT GCC CTT GAC AAT GTC GTG TAA
 S   S   R   A   T   A   L   D   N   V   V   *
```

METHODS OF THERAPY AND DIAGNOSIS USING IMMUNOTARGETING OF CD84HY1-EXPRESSING CELLS

CROSS REFERENCE TO RELATED APPLICATIONS

This application is a continuation-in-part application of U.S. application Ser. No. 10/078,080 filed on Feb. 15, 2002, entitled "Methods of Therapy and Diagnosis Using Immunotargeting of CD84Hy1-expressing Cells," which in turn is a continuation-in-part application of PCT Application Ser. No. PCT/US01/02613 filed Jan. 25, 2001, entitled "Methods and Materials Relating to CD84-like Polypeptides and Polynucleotides," which in turn is a continuation-in-part application of U.S. application Ser. No. 09/645,476 filed on Aug. 24, 2000, entitled "Methods and Materials Relating To CD84-like Polypeptides and Polynucleotides", which is a continuation-in-part application of U.S. application Ser. No. 09/491,404, filed Jan. 25, 2000, entitled "Novel Contigs Obtained from Various Libraries". These and all other U.S. patents and patent applications cited herein are hereby incorporated by reference in their entirety.

TECHNICAL FIELD

This invention relates to compositions and methods for targeting CD84Hy1 protein-expressing cells and their use in the therapy and diagnosis of various pathological states, including cancer, autoimmune disease, organ transplant rejection, and allergic reactions.

BACKGROUND

Antibody therapy for cancer involves the use of antibodies, or antibody fragments, against a tumor antigen to target antigen-expressing cells. Antibodies, or antibody fragments, may have direct or indirect cytotoxic effects or may be conjugated or fused to cytotoxic moieties. Direct effects include the induction of apoptosis, the blocking of growth factor receptors, and anti-idiotype antibody formation. Indirect effects include antibody-dependent cell-mediated cytotoxicity (ADCC) and complement-mediated cellular cytotoxicity (CMCC). When conjugated or fused to cytotoxic moieties, the antibodies, or fragments thereof, provide a method of targeting the cytotoxicity towards the tumor antigen expressing cells. (Green, et al., *Cancer Treatment Reviews*, 26:269-286 (2000), this and all other references cited herein are hereby incorporated by reference in their entirety).

Because antibody therapy targets cells expressing a particular antigen, there is a possibility of cross-reactivity with normal cells or tissue. Although some cells, such as hematopoietic cells, are readily replaced by precursors, cross-reactivity with many tissues can lead to detrimental results. Thus, considerable research has gone towards finding tumor-specific antigens. Such antigens are found almost exclusively on tumors or are expressed at a greater level in tumor cells than the corresponding normal tissue. Tumor-specific antigens provide targets for antibody targeting of cancer, or other disease-related cells, expressing the antigen. Antibodies specific to such tumor-specific antigens can be conjugated to cytotoxic compounds or can be used alone in immunotherapy. Immunotoxins target cytotoxic compounds to induce cell death. For example, anti-CD22 antibodies conjugated to deglycosylated ricin A may be used for treatment of B cell lymphoma that has relapsed after conventional therapy (Amlot, et al., *Blood* 82:2624-2633 (1993)) and has demonstrated encouraging responses in initial clinical studies.

Immunotherapy provides a method of harnessing the immune system to treat various pathological states, including cancer, autoimmune disease, transplant rejection, hyperproliferative conditions, and allergic reactions. The immune system functions to eliminate organisms or cells that are recognized as non-self, including microorganisms, neoplasms and transplants. A cell-mediated host response to tumors includes the concept of immunologic surveillance, by which cellular mechanisms associated with cell-mediated immunity, destroy newly transformed tumor cells after recognizing tumor-associated antigens (antigens associated with tumor cells that are not apparent on normal cells). Furthermore, a humoral response to tumor-associated antigens enables destruction of tumor cells through immunological processes triggered by the binding of an antibody to the surface of a cell, such as antibody-dependent cellular cytotoxicity (ADCC) and complement mediated lysis.

Recognition of an antigen by the immune system triggers a cascade of events including cytokine production, B-cell proliferation, and subsequent antibody production. Often tumor cells have reduced capability of presenting antigen to effector cells, thus impeding the immune response against a tumor-specific antigen. In some instances, the tumor-specific antigen may not be recognized as non-self by the immune system, preventing an immune response against the tumor-specific antigen from occurring. In such instances, stimulation or manipulation of the immune system provides effective techniques of treating cancers expressing one or more tumor-specific antigens.

For example, Rituximab (Rituxan®) is a chimeric antibody directed against CD20, a B cell-specific surface molecule found on >95% of B-cell non-Hodgkin's lymphoma (Press, et al., *Blood* 69:584-591 (1987); Malony, et al., *Blood* 90: 2188 (1997)). Rituximab induces ADCC and inhibits cell proliferation through apoptosis in malignant B cells in vitro (Maloney, et al., *Blood* 88 637a (1996)). Rituximab is currently used as a therapy for advanced stage or relapsed low-grade non-Hodgkin's lymphoma, which has not responded to conventional therapy.

Several cell surface molecules that participate in B-cell and T-cell activation are expressed predominantly in several hematopoietic-based cancers, such as leukemias and lymphomas. A significant number of these molecules, such as CD2 and CD48, belong to the Ig superfamily, which is involved in processes such as adhesion, migration, proliferation, differentiation, and effector function of leukocytes (de la Fuente, et al., *Blood* 90:2398-2405 (1997)). In vivo studies have shown that administration of CD2 and CD48 monoclonal antibodies can inhibit T-cell responses and prolong allograft survival (Gückel, et al., *J. Exp. Med.* 174:957-967 (1991); Qin, et al., *J. Exp. Med.* 179:341-346 (1994)). CD84 is a member of the CD2 family and is expressed on hematopoietic tissues and cells, primarily lymphocytes and monocytes (de la Fuente, et al., supra) and may play a role in leukocyte activation. A CD84 homolog, NTB-A, may function as a co-receptor in inducing Natural Killer (NK) cell-mediated cytotoxicity, and its function was significantly affected in the absence of an intracellular signaling protein, Src homology 2-domain containing protein (Bottino, et al., *J. Exp. Med.* 194:235-246 (2001)).

Active immunotherapy, whereby the host is induced to initiate an immune response against its own tumor cells can be achieved using therapeutic vaccines. One type of tumor-specific vaccine uses purified idiotype protein isolated from tumor cells, coupled to keyhole limpet hemocyanin (KLH) and mixed with adjuvant for injection into patients with low-grade follicular lymphoma (Hsu, et al., *Blood* 89:3129-3135 (1997). Another type of vaccine uses antigen-presenting cells (APCs), which present antigen to naïve T cells during the recognition and effector phases of the immune response. Dendritic cells, one type of APC, can be used in a cellular vaccine in which the dendritic cells are isolated from the patient, co-cultured with tumor antigen and then reinfused as a cellular vaccine (Hsu, et al., *Nat. Med.* 2:52-58 (1996). Immune responses can also be induced by injection of naked DNA. Plasmid DNA that expresses bicistronic mRNA encoding both the light and heavy chains of tumor idiotype proteins, such as those from B cell lymphoma, when injected into mice, are able to generate a protective, anti-tumor response (Singh, et al., *Vaccine* 20:1400-1411 (2002)).

Thus, there exists a need in the art to identify and develop agents, such as peptide fragments, nucleic acids, or antibodies, that provide therapeutic compositions and diagnostic methods for treating and identifying cancer, hyperproliferative disorders, auto-immune diseases, and organ transplant rejection.

SUMMARY OF THE INVENTION

The invention provides therapeutic and diagnostic methods of targeting cells expressing the CD84Hy1 protein by using targeting elements such as CD84Hy1 polypeptides, nucleic acids encoding CD84Hy1 protein, and anti-CD84Hy1 antibodies, including fragments or other modifications thereof. The CD84Hy1 protein is highly expressed in certain hematopoeitic-based cancers but not by most non-hematopoetic, healthy cells. Thus, targeting of cells that express CD84Hy1 will have a minimal effect on healthy tissues while destroying or inhibiting the growth of the hematopoeitic-based cancer cells. Similarly, non-hematopoeitic type tumors (solid tumors) can be targeted if they bear the CD84Hy1 antigen. For example, inhibition of growth and/or destruction of CD84Hy1-expressing cancer cells results from targeting such cells with anti-CD84Hy1 antibodies. One embodiment of the invention is a method of destroying CD84Hy1-expressing cells by conjugating anti-CD84Hy1 antibodies with cytocidal materials such as radioisotopes or other cytotoxic compounds.

The present invention provides a variety of targeting elements and compositions. One such embodiment is a composition comprising an anti-CD84Hy1 antibody preparation. Exemplary antibodies include a single anti-CD84Hy1 antibody, a combination of two or more anti-CD84Hy1 antibodies, a combination of an anti-CD84Hy1 antibody with a non-CD84Hy1 antibody, a combination of anti-CD84Hy1 antibody and a therapeutic agent, a combination of an anti-CD84Hy1 antibody and a cytocidal agent, a bispecific anti-CD84Hy1 antibody, Fab CD84Hy1 antibodies or fragments thereof, including any fragment of an antibody that retains one or more CDRs that recognize CD84Hy1, humanized anti-CD84Hy1 antibodies that retain all or a portion of a CDR that recognizes CD84Hy1, anti-CD84Hy1 conjugates, and anti-CD84Hy1 antibody fusion proteins.

Another targeting embodiment of the invention is a vaccine comprising a CD84Hy1 polypeptide, or a fragment or variant thereof and optionally comprising a suitable adjuvant.

Yet another targeting embodiment is a composition comprising a nucleic acid encoding CD84Hy1, or a fragment or variant thereof, optionally within a recombinant vector. A further targeting embodiment of the present invention is a composition comprising an antigen-presenting cell transformed with a nucleic acid encoding CD84Hy1, or a fragment or variant thereof, optionally within a recombinant vector.

The present invention further provides a method of targeting CD84Hy1-expressing cells, which comprises administering a targeting element or composition in an amount effective to target CD84Hy1-expressing cells. Any one of the targeting elements or compositions described herein may be used in such methods, including an anti-CD84Hy1 antibody preparation, a vaccine comprising a CD84Hy1 polypeptide, or a fragment or variant thereof or a composition of a nucleic acid encoding CD84Hy1, or fragment or variant thereof, optionally within a recombinant vector or a composition of an antigen-presenting cell transformed with a nucleic acid encoding CD84Hy1, or fragment or variant thereof, optionally within a recombinant vector.

The invention also provides a method of inhibiting the growth of hematopoietic-based, CD84Hy1-expressing cancer cells, which comprises administering a targeting element or a targeting composition in an amount effective to inhibit the growth of said hematopoetic-based cancer cells. Any one of the targeting elements or compositions described herein may be used in such methods, including an anti-CD84Hy1 antibody preparation, a vaccine comprising a CD84Hy1 polypeptide, fragment, or variant thereof, composition of a nucleic acid encoding CD84Hy1, or fragment or variant thereof, optionally within a recombinant vector, or a composition of an antigen-presenting cell transformed with a nucleic acid encoding CD84Hy1, or fragment or variant thereof, optionally within a recombinant vector.

The present invention further provides a method of treating disorders associated with the proliferation of CD84Hy1-expressing cells in a subject in need thereof, comprising the step of administering a targeting element or targeting composition in a therapeutically effective amount to treat disorders associated with CD84Hy1-expressing cells. Any one of the targeting elements or compositions described herein may be used in such methods, including an anti-CD84Hy1 antibody preparation, a vaccine comprising a CD84Hy1 polypeptide, fragment, or variant thereof, a composition of a nucleic acid encoding CD84Hy1, or fragment or variant thereof, optionally within a recombinant vector, or a composition of an antigen-presenting cell comprising a nucleic acid encoding CD84Hy1, or fragment or variant thereof, optionally within a recombinant vector. Examples of disorders associated with the proliferation of CD84Hy1-expressing cells include cancers, such as non-Hodgkin's B-cell lymphomas, B-cell leukemias, T-cell leukemias, T-cell lymphomas, chronic lymphocytic leukemia, acute myelogenous leukemia, acute myelomonocytic leukemia, acute lymphoblastic leukemia, chronic myelogenous leukemia, lymphosarcoma leukemia, malignant lymphoma, B cell large cell lymphoma, multiple myeloma, myeloid leukemia, chronic myeloid leukemia, myelodysplastic syndromes, X-linked lymphoproliferative disorders, and Epstein Barr Virus-related conditions such as mononucleosis; autoimmune disease; hyperproliferative disorders; organ transplant rejection; and certain allergic reactions. Non-hematopoietic tumors, such as breast, colon, prostate, squamous cell or epithelial cell carcinomas, that bear the CD84Hy1 antigen can also be targeted.

The invention further provides a method of modulating the immune system by either suppression or stimulation of growth factors and cytokines, by administering the targeting elements or compositions of the invention. The invention also provides a method of modulating the immune system through activation of immune cells (such as natural killer cells, T cells, B cells and myeloid cells), through the suppression of activation, or by stimulating or suppressing proliferation of these cells by CD84Hy1 peptide fragments or CD84Hy1 antibodies.

The present invention thereby provides a method of treating immune-related disorders by suppressing the immune system in a subject in need thereof, by administering the targeting elements or compositions of the invention. Such immune-related disorders include but are not limited to autoimmune disease and organ transplant rejection.

The present invention also provides a method of diagnosing disorders associated with CD84Hy1-expressing cells comprising the step of measuring the expression patterns of CD84Hy1 protein and/or mRNA. Yet another embodiment of a method of diagnosing disorders associated with CD84Hy1-expressing cells comprising the step of detecting CD84Hy1 expression using anti-CD84Hy1 antibodies. Such methods of diagnosis include compositions, kits and other approaches for determining whether a patient is a candidate for CD84Hy1 immunotherapy.

The present invention also provides a method of enhancing the effects of therapeutic agents and adjunctive agents used to treat and manage disorders associated with CD84Hy1-expressing cells, by administering CD84Hy1 preparations with therapeutic and adjuvant agents commonly used to treat such disorders.

BRIEF DESCRIPTION OF THE DRAWING

FIG. 1 depicts the nucleic acid sequence of a cDNA encoding a CD84Hy1 polypeptide (SEQ ID NO: 1) and the amino acid sequence of the encoded polypeptide (SEQ ID NO: 2).

DETAILED DESCRIPTION OF THE INVENTION

The present invention relates to methods of targeting cells that express CD84Hy1 using targeting elements, such as CD84Hy1 polypeptides, nucleic acids encoding CD84Hy1, anti-CD84Hy1 antibodies, including fragments or other modifications of any of these elements.

The present invention provides a novel approach for diagnosing and treating diseases and disorders associated with CD84Hy1-expressing cells. The method comprises administering an effective dose of targeting preparations such as vaccines, antigen presenting cells, or pharmaceutical compositions comprising the targeting elements, CD84Hy1 polypeptides, nucleic acids encoding CD84Hy1, or anti-CD84Hy1 antibodies, described below. Targeting of CD84Hy1 on the cell membranes of CD84Hy1-expressing cells is expected to inhibit the growth of or destroy such cells. An effective dose will be the amount of such targeting CD84Hy1 preparations necessary to target the CD84Hy1 on the cell membrane and/or inhibit the growth of or destroy the CD84Hy1-expressing cells and/or inhibit metastasis.

A further embodiment of the present invention is to enhance the effects of therapeutic agents and adjunctive agents used to treat and manage disorders associated with CD84Hy1-expressing cells, by administering CD84Hy1 preparations with therapeutic and adjuvant agents commonly used to treat such disorders. Chemotherapeutic agents useful in treating neoplastic disease and antiproliferative agents and drugs used for immunosuppression include alkylating agents, such as nitrogen mustards, alkyl sulfonates, nitrosoureas, triazenes; antimetabolites, such as folic acid analogs, pyrimidine analogs, and purine analogs; natural products, such as vinca alkaloids, epipodophyllotoxins, antibiotics, and enzymes; miscellaneous agents such as polatinum coordination complexes, substituted urea, methyl hydrazine derivatives, and adrenocortical suppressant; and hormones and antagonists, such as adrenocorticosteroids, progestins, estrogens, androgens, and anti-estrogens (Calebresi and Parks, pp. 1240-1306, in *The Pharmacological Basis of Therapeutics*, Seventh Edition, Eds. A. G. Goodman, L. S. Goodman, T. W. Rall, and F. Murad, MacMillan Publishing Company, New York, (1985)).

Adjunctive therapy used in the management of such disorders includes, for example, radiosensitizing agents, coupling of antigen with heterologous proteins, such as globulin or beta-galactosidase, or inclusion of an adjuvant during immunization.

High doses may be required for some therapeutic agents to achieve levels to effectuate the target response, but may often be associated with a greater frequency of dose-related adverse effects. Thus, combined use of the immunotherapeutic methods of the present invention with agents commonly used to treat CD84Hy1 protein-related disorders allows the use of relatively lower doses of such agents resulting in a lower frequency of adverse side effects associated with long-term administration of the conventional therapeutic agents. Thus another indication for the immunotherapeutic methods of this invention is to reduce adverse side effects associated with conventional therapy of disorders associated with CD84Hy1-expressing cells.

Definitions

The term "fragment" of a nucleic acid refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to a portion of SEQ ID NO: 1. A polypeptide "fragment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity. The term "immunogenic" refers to the capability of the natural, recombinant or synthetic CD84Hy1-like peptide, or any peptide thereof, to induce a specific immune response in appropriate animals or cells and to bind with specific antibodies.

The term "variant" (or "analog") refers to any polypeptide differing from naturally occurring polypeptides by amino acid insertions, deletions, and substitutions, created using, e.g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Immunotargeting of CD84Hy1

CD84Hy1 polypeptides and polynucleotides encoding such polypeptides are disclosed in co-owned U.S. patent application Ser. Nos. 09/645,476 and 09/491,404. These and all other U.S. patents cited herein are hereby incorporated by reference in their entirety. U.S. patent application Ser. No. 09/491,404 incorporated by reference herein in its entirety relates, in general to a collection or library of at least one novel nucleic acid sequences, specifically contigs, assembled from expressed sequence tags (ESTs). U.S. patent application Ser. No. 09/645,476, incorporated by reference herein in its entirety, (specifically including all sequences in the sequence listing) discloses CD84-like polypeptides, isolated polynucleotides encoding such polypeptides, including recombinant molecules, cloned genes or degenerate variants thereof, especially naturally occurring variants such as allelic variants, fragments or analogs or variants of such polynucleotides or polypeptides, antisense polynucleotide molecules, and antibodies that specifically recognize one or more epitopes present on such polypeptides, including polyclonal, monoclonal, single chain, bispecific, fragment, human and humanized antibodies, as well as hybridomas producing monoclonal antibodies, and diagnostic and therapeutic uses and screening assays associated with such polynucleotides, polypeptides and antibodies. Specifically, the polynucleotides of U.S. patent application Ser. No. 09/645, 476 are based on a CD84-like polynucleotide isolated from a cDNA library prepared from human spleen (Hyseq clone identification numbers 2938352).

The amino acid sequence of an exemplary CD84Hy1 polypeptide and the nucleic acid sequence of the cDNA encoding the polypeptide are provided in FIG. 1 (SEQ ID NOS: 2 and 1, respectively). CD84Hy1 is expressed in certain hematopoeitic-based cancers, while most non-hematopoetic, healthy cells fail to express CD84Hy1 or express it at low levels. Thus, targeting CD84Hy1 will have a minimal effect on healthy tissues while destroying or inhibiting the growth of the hematopoeitic-based cancer cells. In addition, other cancers, such as solid tumors of epithelial and squamous cell origin that express CD84Hy1 will be good targets for CD84Hy1 targeting. CD84Hy1 is also expressed in certain autoimmune disorders, including systemic lupus erythematosus, Hasimoto Thyroiditis, Sjörgen's Syndrome, and pericarditis lupus (see Table 4), thus targeting cells expressing CD84Hy1 will be useful in treating these diseases. Finally, CD84Hy1 is expressed in rejected heart, liver, and kidney tissues, whereas normal tissues do not express CD84Hy1 (see Table 5), thus targeting CD84Hy1 will be useful in reducing and/or eliminating tissue rejection after transplantation.

A. Targeting Using CD84Hy1 Vaccines

In one embodiment, the present invention provides a vaccine comprising a CD84Hy1 polypeptide to stimulate the immune system against CD84Hy1, thus targeting CD84Hy1-expressing cells. Use of a tumor antigen in a vaccine for generating cellular and humoral immunity for the purpose of anti-cancer therapy is well known in the art. For example, one type of tumor-specific vaccine uses purified idiotype protein isolated from tumor cells, coupled to keyhole limpet hemocyanin (KLH) and mixed with adjuvant for injection into patients with low-grade follicular lymphoma (Hsu, et al., *Blood* 89:3129-3135 (1997)). U.S. Pat. No. 6,312,718 describes methods for inducing immune responses against malignant B cells, in particular lymphoma, chronic lymphocytic leukemia, and multiple myeloma. The methods described therein utilize vaccines that include liposomes having (1) at least one B-cell malignancy-associated antigen, (2) IL-2 alone, or in combination with at least one other cytokine or chemokine, and (3) at least one lipid molecule. Methods of vaccinating against CD84Hy1 typically employ a CD84Hy1 polypeptide, including fragments, analogs and variants.

As another example, dendritic cells, one type of antigen-presenting cell, can be used in a cellular vaccine in which the dendritic cells are isolated from the patient, co-cultured with tumor antigen and then reinfused as a cellular vaccine (Hsu, et al., *Nat. Med.* 2:52-58 (1996)).

Combining this vaccine therapy with other types of therapeutic agents or treatments such as chemotherapy or radiation is also contemplated.

B. Targeting Using CD84Hy1 Nucleic Acids

1. Direct Delivery of Nucleic Acids

However, in some embodiments, a nucleic acid encoding CD84Hy1, or encoding a fragment, analog or variant thereof, within a recombinant vector is utilized. Such methods are known in the art. For example, immune responses can be induced by injection of naked DNA. Plasmid DNA that expresses bicistronic mRNA encoding both the light and heavy chains of tumor idiotype proteins, such as those from B cell lymphoma, when injected into mice, are able to generate a protective, anti-tumor response (Singh, et al., *Vaccine* 20:1400-1411 (2002)) CD84Hy1 viral vectors are particularly useful for delivering CD84Hy1-encoding nucleic acids to cells. Examples of vectors include those derived from influenza, adenovirus, vaccinia, herpes simplex virus, fowlpox, vesicular stomatitis virus, canarypox, poliovirus, adeno-associated virus, and lentivirus and sindbus virus. Of course, non-viral vectors, such as liposomes or even naked DNA, are also useful for delivering CD84Hy1-encoding nucleic acids to cells.

Combining this type of therapy with other types of therapeutic agents or treatments such as chemotherapy or radiation is also contemplated.

2. CD84Hy1 Nucleic Acids Expressed in Cells

In some embodiments, a vector comprising a nucleic acid encoding the CD84Hy1 polypeptide (including a fragment, analog or variant) is introduced into a cell, such as a dendritic cell or a macrophage. When expressed in an antigen-presenting cell, CD84Hy1 antigens are presented to T cells eliciting an immune response against CD84Hy1. Such methods are also known in the art. Methods of introducing tumor antigens into antigen presenting cells and vectors useful therefore are described in U.S. Pat. No. 6,300,090. The vector encoding CD84Hy1 may be introduced into the antigen presenting cells in vivo. Alternatively, antigen-presenting cells are loaded with CD84Hy1 or a nucleic acid encoding CD84Hy1 ex vivo and then introduced into a patient to elicit an immune response against CD84Hy1. In another alternative, the cells presenting CD84Hy1 antigen are used to stimulate the expansion of anti-CD84Hy1 cytotoxic T lymphocytes (CTL) ex vivo followed by introduction of the stimulated CTL into a patient. (U.S. Pat. No. 6,306,388). Combining this type of therapy with other types of therapeutic agents or treatments such as chemotherapy or radiation is also contemplated.

C. Anti-CD84Hy1 Antibodies

Alternatively, immunotargeting involves the administration of components of the immune system, such as antibodies, antibody fragments, or primed cells of the immune system against the target. Methods of immunotargeting cancer cells using antibodies or antibody fragments are well known in the art. U.S. Pat. No. 6,306,393 describes the use of anti-CD22 antibodies in the immunotherapy of B-cell malignancies, and U.S. Pat. No. 6,329,503 describes immunotargeting of cells that express serpentine transmembrane antigens.

CD84Hy1 antibodies (including humanized or human monoclonal antibodies or fragments or other modifications thereof, optionally conjugated to cytotoxic agents) may be introduced into a patient such that the antibody binds to CD84Hy1 on the cancer cells and mediates the destruction of the cells and the tumor and/or inhibits the growth of the cells or the tumor. Without intending to limit the disclosure, mechanisms by which such antibodies can exert a therapeutic effect may include complement-mediated cytolysis, antibody-dependent cellular cytotoxicity (ADCC), modulating the physiologic function of CD84Hy1, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis. CD84Hy1 antibodies conjugated to toxic or therapeutic agents, such as radioligands or toxins, may also be used therapeutically to deliver the toxic or therapeutic agent directly to CD84Hy1-bearing tumor cells.

CD84Hy1 antibodies may be used to suppress the immune system in patients receiving organ transplants or in patients with autoimmune diseases such as arthritis or systemic lupus erythematosus. Healthy immune cells would be targeted by these antibodies leading their death and clearance from the system, thus suppressing the immune system.

CD84Hy1 antibodies may be used as antibody therapy for solid tumors which express this antigen. Cancer immunotherapy using antibodies has been previously described for other types of cancer, including but not limited to colon cancer (Arlen, et al., *Crit. Rev. Immunol.* 18: 133-138 (1998)), multiple myeloma (Ozaki, et al., *Blood* 90:3179-3186 (1997); Tsunenari, et al., *Blood* 90:2437-2444 (1997), gastric cancer (Kasprzyk, et al., *Cancer Res.* 52:2771-2776 (1992)), B-cell lymphoma (Funakoshi, et al., *J. Immunther. Emphasis Tumor Immunol.* 19:93-101 (1996)), leukemia (Zhong, et al., *Leuk. Res.* 20:581-589 (1996)), colorectal cancer (Moun, et al., *Cancer Res.* 54:6160-6166 (1994)); Velders, et al., *Cancer Res.* 55:4398-4403 (1995)), and breast cancer (Shepard, et al., *J. Clin. Immunol.* 11:117-127 (1991)).

Although CD84Hy1 antibody therapy may be useful for all stages of the foregoing cancers, antibody therapy may be particularly appropriate in advanced or metastatic cancers. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with CD84Hy1 antibody with tumors resistant to chemotherapeutic agents might induce sensitivity and responsiveness to these agents in combination.

Prior to anti-CD84Hy1 immunotargeting, a patient may be evaluated for the presence and level of CD84Hy1 expression by the cancer cells, preferably using immunohistochemical assessments of tumor tissue, quantitative CD84Hy1 imaging, quantitative RT-PCR, or other techniques capable of reliably indicating the presence and degree of CD84Hy1 expression. For example, a blood or biopsy sample may be evaluated by immunohistochemical methods to determine the presence of CD84Hy1-expressing cells or to determine the extent of CD84Hy1 expression on the surface of the cells within the sample. Methods for immunohistochemical analysis of tumor tissues or released fragments of CD84Hy1 in the serum are well known in the art.

Anti-CD84Hy1 antibodies useful in treating cancers include those, which are capable of initiating a potent immune response against the tumor and those, which are capable of direct cytotoxicity. In this regard, anti-CD84Hy1 mAbs may elicit tumor cell lysis by either complement-mediated or ADCC mechanisms, both of which require an intact Fc portion of the immunoglobulin molecule for interaction with effector cell Fc receptor sites or complement proteins. In addition, anti-CD84Hy1 antibodies that exert a direct biological effect on tumor growth are useful in the practice of the invention. Potential mechanisms by which such directly cytotoxic antibodies may act include inhibition of cell growth, modulation of cellular differentiation, modulation of tumor angiogenesis factor profiles, and the induction of apoptosis. The mechanism by which a particular anti-CD84Hy1 antibody exerts an anti-tumor effect may be evaluated using any number of in vitro assays designed to determine ADCC, ADMMC, complement-mediated cell lysis, and so forth, as is generally known in the art.

The anti-tumor activity of a particular anti-CD84Hy1 antibody, or combination of anti-CD84Hy1 antibody, may be evaluated in vivo using a suitable animal model. For example, xenogenic lymphoma cancer models wherein human lymphoma cells are introduced into immune compromised animals, such as nude or SCID mice. Efficacy may be predicted using assays, which measure inhibition of tumor formation, tumor regression or metastasis, and the like.

It should be noted that the use of murine or other non-human monoclonal antibodies, human/mouse chimeric mAbs may induce moderate to strong immune responses in some patients. In the most severe cases, such an immune response may lead to the extensive formation of immune complexes, which, potentially, can cause renal failure. Accordingly, preferred monoclonal antibodies used in the practice of the therapeutic methods of the invention are those which are either fully human or humanized and which bind specifically to the target CD84Hy1 antigen with high affinity but exhibit low or no antigenicity in the patient.

The method of the invention contemplates the administration of single anti-CD84Hy1 monoclonal antibodies (mAbs) as well as combinations, or "cocktails", of different mAbs. Two or more monoclonal antibodies that bind to CD84Hy1 may provide an improved effect compared to a single antibody. Alternatively, a combination of an anti-CD84Hy1 antibody with an antibody that binds a different antigen may provide an improved effect compared to a single antibody. Such mAb cocktails may have certain advantages inasmuch as they contain mAbs which exploit different effector mechanisms or combine directly cytotoxic mAbs with mAbs that rely on immune effector functionality. Such mAbs in combination may exhibit synergistic therapeutic effects. In addition, the administration of anti-CD84Hy1 mAbs may be combined with other therapeutic agents, including but not limited to various chemotherapeutic agents, androgen-blockers, and immune modulators (e.g., IL-2, GM-CSF). The anti-CD84Hy1 mAbs may be administered in their "naked" or unconjugated form, or may have therapeutic agents conjugated to them. Additionally, bispecific antibodies may be used. Such an antibody would have one antigenic binding domain specific for CD84Hy1 and the other antigenic binding domain specific for another antigen (such as CD20 for example). Finally, Fab CD84Hy1 antibodies or fragments of these antibodies (including fragments conjugated to other protein sequences or toxins) may also be used as therapeutic agents.

(1) Anti-CD84Hy1 Antibodies

Antibodies that specifically bind CD84Hy1 are useful in compositions and methods for immunotargeting cells expressing CD84Hy1 and for diagnosing a disease or disorder wherein cells involved in the disorder express CD84Hy1. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds that include CDR and/or antigen-binding sequences, which specifically recognize. CD84Hy1. Antibody fragments, including Fab, Fab', F(ab')$_2$, and F$_v$, are also useful.

The term "specific for" indicates that the variable regions of the antibodies recognize and bind CD84Hy1 exclusively (i.e., able to distinguish CD84Hy1 from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays in which one can determine binding specificity of an anti-CD84Hy1 antibody are well known and routinely practiced in the art. (Chapter 6 in, *Antibodies A Laboratory Manual*, Eds. Harlow, et al., Cold Spring Harbor Laboratory, Cold Spring Harbor, N.Y. (1988)).

CD84Hy1 polypeptides can be used to immunize animals to obtain polyclonal and monoclonal antibodies that specifically react with CD84Hy1. Such antibodies can be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides have been previously described (Merrifield, *J. Amer. Chem. Soc.* 85:2149-2154 (1963), Krstenansky, et al., *FEBS Lett.* 211:10 (1987)). Techniques for preparing polyclonal and monoclonal antibodies as well as hybridomas capable of producing the desired antibody have also been previously disclosed (Campbell, A. M., *Monoclonal Antibodies Technology: Laboratory Techniques in Biochemistry and Molecular Biology*, Elsevier Science Publishers, Amsterdam, The Netherlands (1984), St. Groth, et al., *J. Immunol.* 35:1-21 (1990), Kohler and Milstein, *Nature* 256:495-497 (1975)), the trioma technique, the human B-cell hybridoma technique (Kozbor, et al., *Immunology Today* 4:72 (1983), Cole, et al., pp. 77-96 in, *Monoclonal Antibodies and Cancer Therapy*, Alan R. Liss, Inc., (1985)).

Any animal capable of producing antibodies can be immunized with a CD84Hy1 peptide or polypeptide. Methods for immunization include subcutaneous or intraperitoneal injection of the polypeptide. The amount of the CD84Hy1 peptide or polypeptide used for immunization depends on the animal that is immunized, antigenicity of the peptide and the site of injection. The CD84Hy1 peptide or polypeptide used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell that produces an antibody with the desired characteristics. These include screening the hybridomas with an ELISA assay, Western blot analysis, or radioimmunoassay (Lutz, et al., *Exp. Cell Res.* 175:109-124 (1988)). Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). Techniques described for the production of single chain antibodies can be adapted to produce single chain antibodies to CD84Hy1 (U.S. Pat. No. 4,946,778).

For polyclonal antibodies, antibody-containing antiserum is isolated from the immunized animal and is screened for the presence of antibodies with the desired specificity using one of the above-described procedures.

Because antibodies from rodents tend to elicit strong immune responses against the antibodies when administered to a human, such antibodies may have limited effectiveness in therapeutic methods of the invention. Methods of producing antibodies that do not produce a strong immune response against the administered antibodies are well known in the art. For example, the anti-CD84Hy1 antibody can be a nonhuman primate antibody. Methods of making such antibodies in baboons are disclosed in WO 91/11465 and Losman, et al., *Int. J. Cancer* 46:310-314 (1990). In one embodiment, the anti-CD84Hy1 antibody is a humanized monoclonal antibody. Methods of producing humanized antibodies have been previously described. (U.S. Pat. Nos. 5,997,867 and 5,985,279, Jones, et al., *Nature* 321:522 (1986), Riechmann et al., *Nature* 332:323(1988), Verhoeyen et al., *Science* 239:1534-1536 (1988), Carter, et al., *Proc. Nat'l Acad. Sci. USA* 89:4285-4289 (1992), Sandhu, *Crit. Rev. Biotech.* 12:437-462 (1992), and Singer, et al., *J. Immun.* 150:2844-2857 (1993)). In another embodiment, the anti-CD84Hy1 antibody is a human monoclonal antibody. Humanized antibodies are produced by transgenic mice that have been engineered to produce human antibodies. Hybridomas derived from such mice will secrete large amounts of human monoclonal antibodies. Methods for obtaining human antibodies from transgenic mice are described in Green, et al., *Nature Genet.* 7:13-21 (1994), Lonberg, et al., *Nature* 368:856 (1994), and Taylor, et al., *Int. Immun.* 6:579-591 (1994).

The present invention also includes the use of anti-CD84Hy1 antibody fragments. Antibody fragments can be prepared by proteolytic hydrolysis of an antibody or by expression in *E. coli* of the DNA coding for the fragment. Antibody fragments can be obtained by pepsin or papain digestion of whole antibodies. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods have been previously described (U.S. Pat. Nos. 4,036,945 and 4,331,647, Nisonoff, et al., *Arch Biochem. Biophys.* 89:230 (1960); Porter, *Biochem. J.* 73:119 (1959), Edelman, et al., *Meth. Enzymol.* 1:422 (1967)). Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody. For example, Fv fragments comprise an association of V$_H$ and V$_L$ chains, which can be noncovalent (Inbar, et al., *Proc. Nat'l Acad. Sci. USA* 69:2659 (1972)). Alternatively, the variable chains can be linked by an intermolecular disulfide bond or cross-linked by chemicals such as glutaraldehyde.

In one embodiment, the Fv fragments comprise V$_H$ and V$_L$ chains that are connected by a peptide linker. These single-chain antigen binding proteins (sFv) are prepared by constructing a structural gene comprising DNA sequences encoding the V$_H$ and V$_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing sFvs have been previously described (U.S. Pat. No. 4,946,778, Whitlow, et al., *Methods: A Companion to Methods in Enzymology* 2:97 (1991), Bird, et al., *Science* 242:423 (1988), Pack, et al., *Bio/Technology* 11:1271 (1993)).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick, et al., *Methods: A Companion to Methods in Enymology* 2:106 (1991); Courtenay-Luck, pp. 166-179 in, *Monoclonal Antibodies: Production, Engineering and Clinical Application*, Eds. Ritter et al., Cambridge University Press (1995); Ward, et al., pp. 137-185 in, *Monoclonal Antibodies: Principles and Applications*, Eds. Birch, et al., Wiley-Liss, Inc. (1995).

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling have been previously disclosed (Sternberger, et al., *J. Histochem. Cytochem.* 18:315 (1970); Bayer, et al., *Meth. Enzym.* 62:308 (1979); Engval, et al., *Immunol.* 109:129 (1972); Goding, *J. Immunol. Meth.* 13:215 (1976)).

The labeled antibodies can be used for in vitro, in vivo, and in situ assays to identify cells or tissues in which CD84Hy1 is expressed. Furthermore, the labeled antibodies can be used to identify the presence of secreted CD84Hy1 in a biological sample, such as a blood, urine, saliva samples.

(2) Anti-CD84Hy1 Antibody Conjugates

The present invention contemplates the use of "naked" anti-CD84Hy1 antibodies, as well as the use of immunoconjugates. Immunoconjugates can be prepared by indirectly conjugating a therapeutic agent such as a cytotoxic agent to an antibody component. Toxic moieties include, for example, plant toxins, such as abrin, ricin, modeccin, viscumin, pokeweed anti-viral protein, saporin, gelonin, momoridin, trichosanthin, barley toxin; bacterial toxins, such as Diptheria toxin, *Pseudomonas* endotoxin and exotoxin, *Staphylococcal* enterotoxin A; fungal toxins, such as α-sarcin, restrictocin; cytotoxic RNases, such as extracellular pancreatic RNases; DNase I (Pastan, et al., *Cell* 47:641 (1986), Goldenberg, *Cancer Journal for Clinicians* 44:43 (1994)), calicheamicin, and radioisotopes, such as $^{32}$P, $^{67}$Cu, $^{77}$As, $^{105}$Rh, $^{109}$Pd, $^{111}$Ag, $^{121}$Sn, $^{131}$I, $^{166}$Ho, $^{177}$Lu, $^{186}$Re, $^{188}$Re, $^{194}$Ir, $^{199}$Au (Illidge, and Brock, *Curr. Pharm. Design* 6:1399-1418 (2000)). In humans, clinical trials are underway utilizing a yttrium-90 conjugated anti-CD20 antibody for B cell lymphomas (*Cancer Chemother. Pharmacol.* 48 (Suppl 1):S91-S95 (2001)). General techniques have been previously described (U.S. Pat. Nos. 6,306,393 and 5,057,313, Shih, et al., *Int. J. Cancer* 41:832-839 (1988); Shih, et al., *Int. J. Cancer* 46:1101-1106 (1990)). The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to affect a controlled oxidation of a portion of its carbohydrate rings to generate aldehyde groups. The oxidation is conveniently effected with glycolytic chemical reagents such as NaIO$_4$, according to conventional procedures. The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to ensure substantially complete conversion of the aldehyde functions to Schiff base groups. A reducing agent, such as $NaBH_4$, $NaBH_3CN$ or the like, is used to effect reductive stabilization of the resultant Schiff base intermediate. The resultant adduct can be purified by passage through a conventional sizing column or ultrafiltration membrane to remove cross-linked dextrans. Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, immunomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct. Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300 or affinity chromatography using one or more CD84Hy1 epitopes.

Alternatively, immunoconjugates can be prepared by directly conjugating an antibody component with a therapeutic agent. The general procedure is analogous to the indirect method of conjugation except that a therapeutic agent is directly attached to an oxidized antibody component. It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP) (Yu, et al., *Int. J. Cancer* 56:244 (1994)). General techniques for such conjugation have been previously described (Wong, *Chemistry of Protein Conjugation and Cross-Linking*, CRC Press (1991); Upeslacis, et al., pp. 187-230 in, *Monoclonal Antibodies: Principles and Applications*, Eds. Birch, et al., Wiley-Liss, Inc. (1995); Price, pp. 60-84 in, *Monoclonal Antibodies: Production, Engineering and Clinical Application*, Eds. Ritter, et al., Cambridge University Press (1995)).

As described above, carbohydrate moieties in the Fc region of an antibody can be used to conjugate a therapeutic agent. However, the Fc region may be absent if an antibody fragment is used as the antibody component of the immunoconjugate. Nevertheless, it is possible to introduce a carbohydrate moiety into the light chain variable region of an antibody or antibody fragment (Leung, et al., *J. Immunol.* 154:5919-5926 (1995); U.S. Pat. No. 5,443,953). The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

(3) Anti-CD84Hy1 Antibody Fusion Proteins

When the therapeutic agent to be conjugated to the antibody is a protein, the present invention contemplates the use of fusion proteins comprising one or more anti-CD84Hy1 antibody moieties and an immunomodulator or toxin moiety. Methods of making antibody fusion proteins have been previously described (U.S. Pat. No. 6,306,393). Antibody fusion proteins comprising an interleukin-2 moiety have also been previously disclosed (Boleti, et al., *Ann. Oncol.* 6:945 (1995), Nicolet, et al., *Cancer Gene Ther.* 2:161 (1995), Becker, et al., *Proc. Nat'l Acad. Sci. USA* 93:7826 (1996), Hank, et al., *Clin. Cancer Res.* 2:1951 (1996), Hu, et al., *Cancer Res.* 56:4998 (1996)). In addition, Yang, et al., *Hum. Antibodies Hybridomas* 6:129 (1995), describe a fusion protein that includes an F(ab')$_2$ fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described (Chaudhary, et al., *Nature* 339:394 (1989), Brinkmann, et al., *Proc. Nat'l Acad. Sci. USA* 88:8616 (1991), Batra, et al., *Proc. Natl. Acad. Sci. USA* 89:5867 (1992), Friedman, et al., *J. Immunol.* 150:3054 (1993), Wels, et al., *Int. J. Can.* 60:137 (1995), Fominaya et al., *J. Biol. Chem.* 271:10560 (1996), Kuan, et al., *Biochemistry* 35:2872 (1996), Schmidt, et al., *Int. J. Can.* 65:538 (1996)). Antibody-toxin fusion proteins containing a diphtheria toxin moiety have been described (Kreitman, et al., *Leukemia* 7:553 (1993), Nicholls, et al., *J. Biol. Chem.* 268:5302 (1993), Thompson, et al., *J. Biol. Chem.* 270:28037 (1995), and Vallera, et al., *Blood* 88:2342 (1996). Deonarain, et al. (*Tumor Targeting* 1:177 (1995)), have described an antibody-toxin fusion protein having an RNase moiety, while Linardou, et al. (*Cell Biophys.* 24-25:243 (1994)), produced an antibody-toxin fusion protein comprising a DNase I component. Gelonin and Staphylococcal enterotoxin-A have been used as the toxin moieties in antibody-toxin fusion proteins (Wang, et al., Abstracts of the 209th ACS National Meeting, Anaheim, Calif., Apr. 2-6, 1995, Part 1, BIOT005; Dohlsten, et al., *Proc. Nat'l Acad. Sci. USA* 91:8945 (1994)).

D. CD84Hy1 Peptides

The CD84Hy1 peptide itself may be used to target toxins or radioisotopes to tumor cells in vivo. CD84Hy1 may be a homophilic adhesion protein which will bind to itself. In this case the extracellular domain of CD84Hy1, or a fragment of this domain, may be able to bind to CD84Hy1 expressed on tumor cells. This peptide fragment then may be used as a means to deliver cytotoxic agents to CD84Hy1 bearing tumor cells. Much like an antibody, these fragments may specifically target cells expressing this antigen. Targeted delivery of these cytotoxic agents to the tumor cells would result in cell death and suppression of tumor growth. An example of the ability of an extracellular fragment binding to and activating its intact receptor (by homophilic binding) has been demonstrated with the CD84 receptor (Martin, et al., *J. Immunol,* 167:3668-3676 (2001)).

Extracellular fragments of the CD84Hy1 receptor may also be used to modulate immune cells expressing the protein. Extracellular domain fragments of the receptor may bind to and activate its own receptor expressed on the cell surface. On cells bearing the CD84Hy1 receptor (such as NK cells, T cells, B cells and myeloid cells) this may result in stimulating the release of cytokines (such as interferon gamma for example) that may enhance or suppress the immune system. Additionally, binding of these fragments to cells bearing the CD84Hy1 receptor may result in the activation of these cells and also may stimulate proliferation. Some fragments may bind to the intact CD84Hy1 receptor and block activation signals and cytokine release by immune cells. These fragments would then have an immune suppressive effect. Fragments that activate and stimulate the immune system may have anti-tumor properties. These fragments may stimulate an immunological response that can result in immune mediated tumor cell killing. The same fragments may result in stimulating the immune system to mount an enhance response to foreign invaders such as virus and bacteria. Fragments that suppress the immune response may be useful in treating lymphoproliferative disorders, auto-immune disease, graft-vs-host disease, and inflammatory disorders such as emphysema.

Diseases Amenable to Anti-CD84Hy1 Immunotargeting

In one aspect, the present invention provides reagents and methods useful for treating diseases and conditions wherein cells associated with the disease or disorder express CD84Hy1. These diseases can include cancers, and other hyperproliferative conditions, such as hyperplasia, psoriasis, contact dermatitis, immunological disorders, and infertility. Whether the cells associated with a disease or condition express CD84Hy1 can be determined using the diagnostic methods described herein.

Comparisons of CD84Hy1 mRNA and protein expression levels between diseased cells, tissue or fluid (blood, lymphatic fluid, etc.) and corresponding normal samples are made to determine if the patient will be responsive to CD84Hy1 immunotherapy. Methods for detecting and quantifying the expression of CD84Hy1 mRNA or protein use standard nucleic acid and protein detection and quantitation techniques that are well known in the art and are described in Sambrook, et al., *Molecular Cloning: A Laboratory Manual*, Cold Spring Harbor Laboratory, NY (1989) and Ausubel, et al., *Current Protocols in Molecular Biology*, John Wiley & Sons, New York, N.Y. (1989), both of which are incorporated herein by reference in their entirety. Standard methods for the detection and quantification of CD84Hy1 mRNA include in situ hybridization using labeled CD84Hy1 riboprobes (Gemou-Engesaeth, et al., *Pediatrics* 109: E24-E32 (2002)), Northern blot and related techniques using CD84Hy1 polynucleotide probes (Kunzli, et al., *Cancer* 94:228 (2002)), RT-PCR analysis using CD84Hy1-specific primers (Angchaiskisiri, et al., *Blood* 99:130 (2002)), and other amplification detection methods, such as branched chain DNA solution hybridization assay (Jardi, et al., *J. Viral Hepat.* 8:465-471 (2001)), transcription-mediated amplification (Kimura, et al., *J. Clin. Microbiol.* 40:439-445 (2002)), microarray products, such as oligos, cDNAs, and monoclonal antibodies, and real-time PCR (Simpson, et al., *Molec. Vision,* 6:178-183 (2000)). Standard methods for the detection and quantification of CD84Hy1 protein include western blot analysis (Sambrook, et al., *Molecular Cloning: A Laboratory Manual*, Cold Spring Harbor Laboratory, NY (1989); Ausubel, et al., *Current Protocols in Molecular Biology*, John Wiley & Sons, New York, N.Y. (1989)), immunocytochemistry (Racila, et al., *Proc. Natl. Acad. Sci. USA* 95:4589-4594 (1998)), and a variety of immunoassays, including enzyme-linked immunosorbant assay (ELISA), radioimmuno assay (RIA), and specific enzyme immunoassay (EIA) (Sambrook, et al., *Molecular Cloning: A Laboratory Manual*, Cold Spring Harbor Laboratory, NY (1989); or Ausubel, et al., *Current Protocols in Molecular Biology*, John Wiley & Sons, New York, N.Y. (1989)). Peripheral blood cells can also be analyzed for CD84Hy1 expression using flow cytometry using, for example, immunomagnetic beads specific for CD84Hy1 (Racila, et al., *Proc. Natl. Acad. Sci. USA* 95:4589-4594 (1998)) or biotinylated CD84Hy1 antibodies (Soltys, et al., *J. Immunol.* 168:1903 (2002)). Tumor aggressiveness can be gauged by determining the levels of CD84Hy1 protein or mRNA in tumor cells compared to the corresponding normal cells (Orlandi, et al., *Cancer Res.* 62:567 (2002)). In one embodiment, the disease or disorder is a cancer. Cancer, a leading cause of death in the United States, causes over a half-million deaths annually. As the population ages, the numbers of deaths due to cancer are expected to rise significantly. Cancer is a general term and encompasses various types of malignant neoplasms, most of which invade surrounding tissues, may metastasize to several sites, and are likely to recur after attempted removal and to cause death of the patient unless adequately treated. Cancer can develop in any tissue of any organ at any age. Once a cancer diagnosis is made, treatment decisions are paramount. Successful therapy focuses on the primary tumor and its metastases. Various types of cancer treatments have been developed to improve the survival and quality of life of cancer patients. Advances in cancer treatment include new cytotoxic agents and new surgical and radiotherapy techniques. However, many of these treatments have substantial emotional and physical drawbacks. Furthermore, treatment failure remains a common occurrence. Such shortcomings have driven cancer researchers and caregivers to develop new and effective ways of treating cancer.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed "malignant" and may lead to death of the organism. Malignant neoplasms or "cancers" are distinguished from benign growths in that, in addition to exhibiting aggressive cellular proliferation, they may invade surrounding tissues and metastasize. Moreover, malignant neoplasms are characterized in that they show a greater loss of differentiation (greater "dedifferentiation"), and greater loss of their organization relative to one another and their surrounding tissues. This property is also called "anaplasia."

Neoplasms treatable by the present invention also include solid phase tumors/malignancies, i.e., carcinomas, locally advanced tumors and human soft tissue sarcomas. Carcinomas include those malignant neoplasms derived from epithelial cells that infiltrate (invade) the surrounding tissues and give rise to metastastic cancers, including lymphatic metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells that may be amenable to treatment according to the invention include, for example, acute lymphocytic leukemia, acute nonlymphocytic leukemia, chronic lymphocytic leukemia, chronic myelocytic leukemia, cutaneous T-cell lymphoma, hairy cell leukemia, acute myeloid leukemia, erythroleukemia, chronic myeloid (granulocytic) leukemia, Hodgkin's disease, and non-Hodgkin's lymphoma, gastrointestinal cancers including esophageal cancer, stomach cancer, colon cancer, colorectal cancer, polyps associated with colorectal neoplasms, pancreatic cancer and gallbladder cancer, cancer of the adrenal cortex, ACTH-producing tumor, bladder cancer, brain cancer including intrinsic brain tumors, neuroblastomas, astrocytic brain tumors, gliomas, and metastatic tumor cell invasion of the central nervous system, Ewing's sarcoma, head and neck cancer including mouth cancer and larynx cancer, kidney cancer including renal cell carcinoma, liver cancer, lung cancer including small and non-small cell lung cancers, malignant peritoneal effusion, malignant pleural effusion, skin cancers including malignant melanoma, tumor progression of human skin keratinocytes, squamous cell carcinoma, basal cell carcinoma, and hemangiopericytoma, mesothelioma, Kaposi's sarcoma, bone cancer including osteomas and sarcomas such as fibrosarcoma and osteosarcoma, cancers of the female reproductive tract including uterine cancer, endometrial cancer, ovarian cancer, ovarian (germ cell) cancer and solid tumors in the ovarian follicle, vaginal cancer, cancer of the vulva, and cervical cancer; breast cancer (small cell and ductal), penile cancer, prostate cancer, retinoblastoma, testicular cancer, thyroid cancer, trophoblastic neoplasms, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any cancer derived from any organ system. As demonstrated in Examples 1-3, CD84Hy1 is highly expressed in primary B cells and B-cell related disorders. Leukemias can result from uncontrolled B cell proliferation initially within the bone marrow before disseminating to the peripheral blood, spleen, lymph nodes and finally to other tissues. Uncontrolled B cell proliferation also may result in the development of lymphomas that arise within the lymph nodes and then spread to the blood and bone marrow. Immunotargeting CD84Hy1 is use in treating B cell malignancies, leukemias, lymphomas and myelomas including but not limited to multiple myeloma, Burkitt's lymphoma, cutaneous B cell lymphoma, primary follicular cutaneous B cell lymphoma, B lineage acute lymphoblastic leukemia (ALL), B cell non-Hodgkin's lymphoma (NHL), B cell chronic lymphocytic leukemia (CLL), acute lymphoblastic leukemia, hairy cell leukemia (HCL), acute myelogenous leukemia, acute myelomonocytic leukemia, chronic myelogenous leukemia, lymphosarcoma cell leukemia, splenic marginal zone lymphoma, diffuse large B cell lymphoma, B cell large cell lymphoma, malignant lymphoma, prolymphocytic leukemia (PLL), lymphoplasma cytoid lymphoma, mantle cell lymphoma, mucosa-associated lymphoid tissue (MALT) lymphoma, primary thyroid lymphoma, intravascular malignant lymphomatosis, splenic lymphoma, Hodgkin's disease, and intragraft angiotropic large-cell lymphoma. Expression of CD84Hy1 has also been demonstrated in Example 1 and 2 in myeloid leukemia cell lines and tissue, T cell leukemia cell lines and T cell lymphoma tissues and may be treated with CD84Hy1 antibodies. Other diseases that may be treated by the methods of the present invention include multicentric Castleman's disease, primary amyloidosis, Franklin's disease, Seligmann's disease, primary effusion lymphoma, post-transplant lymphoproliferative disease (PTLD) [associated with EBV infection.], paraneoplastic pemphigus, chronic lymphoproliferative disorders, X-linked lymphoproliferative syndrome (XLP), acquired angioedema, angioimmunoblastic lymphadenopathy with dysproteinemia, Herman's syndrome, post-splenectomy syndrome, congenital dyserythropoietic anemia type III, lymphoma-associated hemophagocytic syndrome (LAHS), necrotizing ulcerative stomatitis, Kikuchi's disease, lymphomatoid granulomatosis, Richter's syndrome, polycythemic vera (PV), Gaucher's disease, Gougerot-Sjogren syndrome, Kaposi's sarcoma, cerebral lymphoplasmocytic proliferation (Bind and Neel syndrome), X-linked lymphoproliferative disorders, pathogen associated disorders such as mononucleosis (Epstein Barr Virus), lymphoplasma cellular disorders, post-transplantational plasma cell dyscrasias, and Good's syndrome.

Autoimmune diseases can be associated with hyperactive B cell activity that results in autoantibody production. Inhibition of the development of autoantibody-producing cells or proliferation of such cells may be therapeutically effective in decreasing the levels of autoantibodies in autoimmune diseases including but not limited to systemic lupus erythematosus, Crohn's Disease, graft-verses-host disease, Graves' disease, myasthenia gravis, autoimmune hemolytic anemia, autoimmune thrombocytopenia, asthma, cryoglubulinemia, primary biliary sclerosis, pernicious anemia, Waldenstrom macroglobulinemia, hyperviscosity syndrome, macroglobulinemia, cold agglutinin disease, monoclonal gammopathy of undetermined origin, anetoderma and POEMS syndrome (polyneuropathy, organomegaly, endocrinopathy, M component, skin changes), connective tissue disease, multiple sclerosis, cystic fibrosis, rheumatoid arthritis, autoimmune pulmonary inflammation, psoriasis, Guillain-Barre syndrome, autoimmune thyroiditis, insulin dependent diabetes mellitus, autoimmune inflammatory eye disease, Goodpasture's disease, Rasmussen's encephalitis, dermatitis herpetiformis, thyoma, autoimmune polyglandular syndrome type 1, primary and secondary membranous nephropathy, cancer-associated retinopathy, autoimmune hepatitis type 1, mixed cryoglobulinemia with renal involvement, cystoid macular edema, endometriosis, IgM polyneuropathy (including Hyper IgM syndrome), demyelinating diseases, angiomatosis, and monoclonal gammopathy. As shown in Table 4, immunohistochemical analysis showed CD84Hy1 expression on tissues from the following autoimmune disorders: systemic lupus erythematosus, Hasimoto thyroiditis, Sjorgen syndrome, and pericarditis lupus. Therefore, targeting CD84Hy1 will be useful in treating these and other autoimmune disorders.

Immunotargeting CD84Hy1 may also be useful in the treatment of allergic reactions and conditions e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis, allergic gastroenteropathy, inflammatory bowel disorder (IBD), and contact allergies, such as asthma (particularly allergic asthma), or other respiratory problems.

Immunotargeting CD84Hy1 may also be useful in the management or prevention of transplant rejection in patients in need of transplants such as stem cells, tissue or organ transplant. Thus, one aspect of the invention may find therapeutic utility in various diseases (such as those usually treated with transplantation, including without limitation, aplastic anemia and paroxysmal nocturnal hemoglobinuria) as wells in repopulating the stem cell compartment post irridiation/chemotherapy, either in vivo or ex vivo (i.e. in conjunction with bone marrow transplantation or with peripheral progenitor cell transplantation (homologous or heterologous) as normal cells or genetically manipulated for gene therapy. As shown in Table 5, immunohistochemical analysis showed CD84Hy1 is expressed in rejected heart, liver, and kidney tissue after transplantation, as opposed to normal tissue. Thus, targeting of CD84Hy1 may be useful to prevent and/or reduce tissue rejection after transplantation.

Immunotargeting CD84Hy1 may also be possible to modulate immune responses, in a number of ways. Down regulation may be in the form of inhibiting or blocking an immune response already in progress or may involve preventing the induction of an immune response. Down regulating or preventing one or more antigen functions (including without limitation B lymphocyte antigen functions (such as, for example, CD84Hy1)), e.g., modulating or preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells (i.e. cytotoxic T lymphocytes), followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of therapeutic compositions of the invention on the development of that disease.

Administration

The anti-CD84Hy1 monoclonal antibodies used in the practice of a method of the invention may be formulated into pharmaceutical compositions comprising a carrier suitable for the desired delivery method. Suitable carriers include any material which when combined with the anti-CD84Hy1 antibodies retains the anti-tumor function of the antibody and is nonreactive with the subject's immune systems. Examples include, but are not limited to, any of a number of standard pharmaceutical carriers such as sterile phosphate buffered saline solutions, bacteriostatic water, and the like.

The anti-CD84Hy1 antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises anti-CD84Hy1 mAbs in a solution of preserved bacteriostatic water, sterile unpreserved water, and/or diluted in polyvinylchloride or polyethylene bags containing 0.9% sterile Sodium Chloride for Injection, USP. The anti-CD84Hy1 mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-CD84Hy1 antibody preparation via an acceptable route of administration such as intravenous injection (IV), typically at a dose in the range of about 0.1 to about 10 mg/kg body weight; however other exemplary doses in the range of 0.01 mg/kg to about 100 mg/kg are also contemplated. Doses in the range of 10-500 mg mAb per week may be effective and well tolerated. Rituximab (Rituxan®), a chimeric CD20 antibody used to treat B-cell lymphoma, non-Hodgkin's lymphoma, and relapsed indolent lymphoma, is typically administered at 375 mg/m$^2$ by IV infusion once a week for 4 to 8 doses. Sometimes a second course is necessary, but no more than 2 courses are allowed. An effective dosage range for Rituxan® would be 50 to 500 mg/m$^2$ (Maloney, et al., *Blood* 84: 2457-2466 (1994); Davis, et al., *J. Clin. Oncol.* 18: 3135-3143 (2000)). Based on clinical experience with Trastuzumab (Herceptin®), a humanized monoclonal antibody used to treat HER2(human epidermal growth factor 2)-positive metastatic breast cancer (Slamon, et al., *Mol Cell Biol.* 9:1165 (1989)), an initial loading dose of approximately 4 mg/kg patient body weight IV followed by weekly doses of about 2 mg/kg IV of the anti-CD84Hy1 mAb preparation may represent an acceptable dosing regimen (Slamon, et al., *N. Engl. J. Med.* 344:783 (2001)). Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the mAb or mAbs used, the degree of CD84Hy1 overexpression in the patient, the extent of circulating shed CD84Hy1 antigen, the desired steady-state antibody concentration level, frequency of treatment, and the influence of chemotherapeutic agents used in combination with the treatment method of the invention.

Treatment can also involve anti-CD84Hy1 antibodies conjugated to radioisotopes. Studies using radiolabeled-anticarcinoembryonic antigen (anti-CEA) monoclonal antibodies, provide a dosage guideline for tumor regression of 2-3 infusions of 30-80 mCi/m$^2$ (Behr, et al. *Clin. Cancer Res.* 5(10 Suppl.): 3232s-3242s (1999); Juweid, et al., *J. Nucl. Med.* 39: 34-42 (1998)).

Alternatively, dendritic cells transfected with mRNA encoding CD84Hy1 can be used as a vaccine to stimulate T-cell mediated anti-tumor responses. Studies with dendritic cells transfected with prostate-specific antigen mRNA suggest a 3 cycles of intravenous administration of $1 \times 10^7$-$5 \times 10^7$ cells for 2-6 weeks concomitant with an intradermal injection of $10^7$ cells may provide a suitable dosage regimen (Heiser, et al., *J. Clin. Invest.* 109:409-417 (2002); Hadzantonis and O'Neill, *Cancer Biother. Radiopharm.* 1:11-22 (1999)). Other exemplary doses of between $1 \times 10^5$ to $1 \times 10^9$ cells or $1 \times 10^6$ to $1 \times 10^8$ cells are also contemplated.

Naked DNA vaccines using plasmids encoding CD84Hy1 can induce an immunologic anti-tumor response. Patent application WO200188200-A2 teaches the use of naked DNA vaccines by particle bombardment technique where Ly-9 (a member of the Ig superfamily) DNA-coated microprojectiles at high velocity are used to pierce cell membranes and enter cells without killing the cells. Administration of naked DNA by direct injection into the skin and muscle is not associated with limitations encountered using viral vectors, such as the development of adverse immune reactions and risk of insertional mutagenesis (Hengge, et al., *J. Invest. Dermatol.* 116:979 (2001)). Studies have shown that direct injection of exogenous cDNA into muscle tissue results in a strong immune response and protective immunity (Ilan, *Curr. Opin. Mol. Ther.* 1:116-120 (1999)). Physical (gene gun, electroporation) and chemical (cationic lipid or polymer) approaches have been developed to enhance efficiency and target cell specificity of gene transfer by plasmid DNA (Nishikawa and Huang, *Hum. Gene Ther.* 12:861-870 (2001)). Plasmid DNA can also be administered to the lungs by aerosol delivery (Densmore, et al., *Mol. Ther.* 1:180-188 (2000)). Gene therapy by direct injection of naked or lipid-coated plasmid DNA is envisioned for the prevention, treatment, and cure of diseases such as cancer, acquired immunodeficiency syndrome, cystic fibrosis, cerebrovascular disease, and hypertension (Prazeres, et al., *Trends Biotechnol.* 17:169-174 (1999); Weihl, et al., *Neurosurgery* 44:239-252 (1999)). HIV-1 DNA vaccine dose-escalating studies indicate administration of 30-300 µg/dose as a suitable therapy (Weber, et al., *Eur. J. Clin. Microbiol. Infect. Dis.* 20:800-803 (2001)). Naked DNA injected intracerebrally into the mouse brain was shown to provide expression of a reporter protein, wherein expression was dose-dependent and maximal for 150 µg DNA injected (Schwartz, et al., *Gene Ther.* 3(5):405-411 (1996)) Gene expression in mice after intramuscular injection of nanospheres containing 1 microgram of beta-galactosidase plasmid was greater and more prolonged than was observed after an injection with an equal amount of naked DNA or DNA complexed with Lipofectamine (Truong, et al., *Hum. Gene Ther.* 9(12):1709-1717 (1998)). In a study of plasmid-mediated gene transfer into skeletal muscle as a means of providing a therapeutic source of insulin, wherein four plasmid constructs comprising a mouse furin cDNA transgene and rat proinsulin cDNA were injected into the calf muscles of male Balb/c mice, the optimal dose for most constructs was 100 micrograms plasmid DNA (Kon, et al., *J. Gene Med.* 1:186-194 (1999)). Other exemplary doses of 1-1000 µg/dose or 10-500 µg/dose are also contemplated.

Optimally, patients should be evaluated for the level of circulating shed CD84Hy1 antigen in serum in order to assist in the determination of the most effective dosing regimen and related factors. Such evaluations may also be used for monitoring purposes throughout therapy, and may be useful to gauge therapeutic success in combination with evaluating other parameters.

(1) CD84Hy1 Targeting Compositions

Compositions for targeting CD84Hy1-expressing cells are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount an antibody, or a fragment, variant, derivative or fusion thereof as described herein, in admixture with a pharmaceutically acceptable agent. Typically, the CD84Hy1 immunotargeting agent will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (*Remington's Pharmaceutical Sciences*, 18th Edition, A. R. Gennaro, Ed., Mack Publishing Company, (1990)).

The optimal pharmaceutical composition will be determined by one skilled in the art depending upon, for example, the intended route of administration, delivery format, and desired dosage. See, for example, *Remington's Pharmaceutical Sciences*, supra. Such compositions may influence the physical state, stability, rate of in vivo release, and rate of in vivo clearance of the CD84Hy1 immunotargeting agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefor. In one embodiment of the present invention, CD84Hy1 immunotargeting agent compositions may be prepared for storage by mixing the selected composition having the desired degree of purity with optional formulation agents (*Remington's Pharmaceutical Sciences*, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. The preparation of such pharmaceutically acceptable compositions is within the skill of the art. The formulation components are present in concentrations that are acceptable to the site of administration. For example, buffers are used to maintain the composition at physiological pH or at slightly lower pH, typically within a pH range of from about 5 to about 8. When parenteral administration is contemplated, the therapeutic compositions for use in this invention may be in the form of a pyrogen-free, parenterally acceptable aqueous solution comprising the CD84Hy1 immunotargeting agent in a pharmaceutically acceptable vehicle. A particularly suitable vehicle for parenteral injection is sterile distilled water in which a CD84Hy1 immunotargeting agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a CD84Hy1 immunotargeting agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, CD84Hy1 immunotargeting agents that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethylcellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the CD84Hy1 immunotargeting agent may be dissolved or suspended in suitable liquids, such as fatty oils, liquid, or liquid polyethylene glycol with or without stabilizers.

Another pharmaceutical composition may involve an effective quantity of CD84Hy1 immunotargeting agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving CD84Hy1 immunotargeting agents in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., *Biopolymers,* 22:547-556 (1983)), poly (2-hydroxyethyl-methacrylate) (Langer et al., *J Biomed Mater Res,* 15:167-277, (1981)) and (Langer et al., *Chem Tech,* 12:98-105 (1982)), ethylene vinyl acetate (Langer et al., supra) or poly-D (−)-3-hydroxybutyric acid (EP 133,988). Sustained-release compositions also include liposomes, which can be prepared by any of several methods known in the art. See e.g., Eppstein et al., *Proc Natl Acad Sci* (*USA*), 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried CD84Hy1 immunotargeting agent and a second container having an aqueous formulation. Also included within the scope of this invention are kits containing single and multi-chambered pre-filled syringes (e.g., liquid syringes and lyosyringes).

(2) Dosage

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which CD84Hy1 immunotargeting agent is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 0.01 mg/kg to 1 g/kg; or 1 mg/kg up to about 100 mg/kg or 5 mg/kg up to about 100 mg/kg. In other embodiments, the dosage may range from 10 mCi to 100 mCi per dose for radioimmunotherapy, from about $1\times10^7$ to $5\times10^7$ cells or $1\times10^5$ to $1\times10^9$ cells or $1\times10^6$ to $1\times10^8$ cells per injection or infusion, or from 30 μg to 300 μg naked DNA per dose or 1-1000 μg/dose or 10-500 μg/dose, depending on the factors listed above.

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the CD84Hy1 immunotargeting agent in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

(3) Routes of Administration

The route of administration of the pharmaceutical composition is in accord with known methods, e.g. orally, through injection by intravenous, intraperitoneal, intracerebral (intra-parenchymal), intracerebroventricular, intramuscular, intra-ocular, intra-arterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the CD84Hy1 immunotargeting agent has been absorbed or encapsulated. Where an implantation device is used, the device may be implanted into any suitable tissue or organ, and delivery of the CD84Hy1 immunotargeting agent may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a CD84Hy1 immunotargeting agent can be delivered by implanting certain cells that have been genetically engineered to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapy

CD84Hy1 targeting agents of the invention can be utilized in combination with other therapeutic agents. These other therapeutics include, for example radiation treatment, chemotherapeutic agents, as well as other growth factors.

In one embodiment, anti-CD84Hy1 antibody is used as a radiosensitizer. In such embodiments, the anti-CD84Hy1 antibody is conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin(r), benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Chemotherapy treatment can employ anti-neoplastic agents including, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy with growth factors can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other compositions can include known angiopoietins, for example, vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor, stem cell factor receptor, transforming growth factor, transforming growth factor, transforming growth factor 1, transforming growth factor 1.2, transforming growth factor 2, transforming growth factor 3, transforming growth factor 5, latent transforming growth factor 1, transforming growth factor binding protein I, transforming growth factor binding protein II, transforming growth factor binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Diagnostic Uses of CD84Hy1s (1) Assays for Determining CD84Hy1-Expression Status Determining the status of CD84Hy1 expression patterns in an individual may be used to diagnose cancer and may provide prognostic information useful in defining appropriate therapeutic options. Similarly, the expression status of CD84Hy1 may provide information useful for predicting susceptibility to particular disease stages, progression, and/or tumor aggressiveness. The invention provides methods and assays for determining CD84Hy1 expression status and diagnosing cancers that express CD84Hy1.

In one aspect, the invention provides assays useful in determining the presence of cancer in an individual, comprising detecting a significant increase in CD84Hy1 mRNA or protein expression in a test cell or tissue or fluid sample relative to expression levels in the corresponding normal cell or tissue. In one embodiment, the presence of CD84Hy1 mRNA is evaluated in tissue samples of a lymphoma. The presence of significant CD84Hy1 expression may be useful to indicate whether the lymphoma is susceptible to CD84Hy1 immunotargeting. In a related embodiment, CD84Hy1 expression status may be determined at the protein level rather than at the nucleic acid level. For example, such a method or assay would comprise determining the level of CD84Hy1 expressed by cells in a test tissue sample and comparing the level so determined to the level of CD84Hy1 expressed in a corresponding normal sample. In one embodiment, the presence of CD84Hy1 is evaluated, for example, using immunohistochemical methods. CD84Hy1 antibodies capable of detecting CD84Hy1 expression may be used in a variety of assay formats well known in the art for this purpose.

Peripheral blood may be conveniently assayed for the presence of cancer cells, including lymphomas and leukemias, using RT-PCR to detect CD84Hy1 expression. The presence of RT-PCR amplifiable CD84Hy1 mRNA provides an indication of the presence of one of these types of cancer. A sensitive assay for detecting and characterizing carcinoma cells in blood may be used (Racila, et al., *Proc. Natl. Acad. Sci. USA* 95:4589-4594 (1998)). This assay combines immunomagnetic enrichment with multiparameter flow cytometric and immunohistochemical analyses, and is highly sensitive for the detection of cancer cells in blood, reportedly capable of detecting one epithelial cell in 1 ml of peripheral blood.

A related aspect of the invention is directed to predicting susceptibility to developing cancer in an individual. In one embodiment, a method for predicting susceptibility to cancer comprises detecting CD84Hy1 mRNA or CD84Hy1 in a tissue sample, its presence indicating susceptibility to cancer, wherein the degree of CD84Hy1 mRNA expression present is proportional to the degree of susceptibility.

Yet another related aspect of the invention is directed to methods for gauging tumor aggressiveness (Orlandi, et al., *Cancer Res.* 62:567 (2002)). In one embodiment, a method for gauging aggressiveness of a tumor comprises determining the level of CD84Hy1 mRNA or CD84Hy1 protein expressed by cells in a sample of the tumor, comparing the level so determined to the level of CD84Hy1 mRNA or CD84Hy1 protein expressed in a corresponding normal tissue taken from the same individual or a normal tissue reference sample, wherein the degree of CD84Hy1 mRNA or CD84Hy1 protein expression in the tumor sample relative to the normal sample indicates the degree of aggressiveness.

Methods for detecting and quantifying the expression of CD84Hy1 mRNA or protein are described herein and use standard nucleic acid and protein detection and quantification technologies well known in the art. Standard methods for the detection and quantification of CD84Hy1 mRNA include in situ hybridization using labeled CD84Hy1 riboprobes (Gemou-Engesaeth, et al., *Pediatrics,* 109: E24-E32 (2002)), Northern blot and related techniques using CD84Hy1 polynucleotide probes (Kunzli, et al., *Cancer* 94:228 (2002)), RT-PCR analysis using primers specific for CD84Hy1 (Angchaiskisiri, et al., *Blood* 99:130 (2002)), and other amplification type detection methods, such as, for example, branched DNA (Jardi, et al., *J. Viral Hepat.* 8:465-471 (2001)), SISBA, TMA (Kimura, et al., *J. Clin. Microbiol.* 40:439-445 (2002)), and microarray products of a variety of sorts, such as oligos, cDNAs, and monoclonal antibodies. In a specific embodiment, real-time RT-PCR may be used to detect and quantify CD84Hy1 mRNA expression (Simpson, et al., *Molec. Vision* 6:178-183 (2000)) as described in the Examples, which follow. Standard methods for the detection and quantification of protein may be used for this purpose. In a specific embodiment, polyclonal or monoclonal antibodies specifically reactive with the wild-type CD84Hy1 may be used in an immunohistochemical assay of biopsied tissue (Ristimaki, et al., *Cancer Res.* 62:632 (2002)).

(2) Medical Imaging

CD84Hy1 antibodies and fragments thereof are useful in medical imaging of sites expressing CD84Hy1. Such methods involve chemical attachment of a labeling or imaging agent, such as a radioisotope, which include $^{67}$Cu, $^{90}$Y, $^{125}$I, $^{131}$I, $^{186}$Re, $^{188}$Re, $^{211}$At, $^{212}$Bi, administration of the labeled antibody and fragment to a subject in a pharmaceutically acceptable carrier, and imaging the labeled antibody and fragment in vivo at the target site. Radiolabelled anti-CD84Hy1 antibodies or fragments thereof may be particularly useful in in vivo imaging of CD84Hy1 expressing cancers, such as lymphomas or leukemias. Such antibodies may provide highly sensitive methods for detecting metastasis of CD84Hy1-expressing cancers.

Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1

Cell Lines of Lymphoma and Leukemia Origin Express High Levels of CD84Hy1 mRNA

Expression of CD84Hy1 was determined in various lymphoid and myeloid cell lines. Poly-A messenger RNA was isolated from the cell lines listed in Table 1 and subjected to quantitative, real-time PCR analysis (Simpson, et al., *Molec. Vision.* 6:178-183 (2000)) to determine the relative copy number of CD84Hy1 mRNA expressed per cell in each line. Elongation factor 1 gene expression was used as a positive control and normalization factors in all samples.

All assays were performed in duplicate with the resulting values averaged and expressed as "−" for samples with no detectable CD84Hy1 mRNA in that sample to "+++" for samples with the highest mRNA copy number for CD84Hy1. The following quantitation scale for the real-time PCR experiments was used: "−"=0 copies/cell; "+"=approximately 1-10 copies/cell; "++"=approximately 11-50 copies/cell; and "+++"=approximately >50 copies/cell. The results are indicated in Table 1.

TABLE 1

| Cell Line | CD84Hy1 mRNA Expression |
|---|---|
| Burkitt's Lymphoma (CA46) cell line | ++ |
| Diffuse Lymphoma (HT) cell line | ++ |
| Multiple Myeloma (RPMI) cell line | − |
| Multiple Myeloma (U266B1) cell line | +++ |
| Burkitt's Lymphoma (GA-10) cell line | + |
| Burkitt's Lymphoma (RA1) cell line | +++ |
| Burkitt's Lymphoma (ST486) cell line | + |
| B Lymphoma (RL) cell line | + |
| Chronic Myeloid Leukemia (K562) cell line | − |
| Acute Myeloid Leukemia (KG-1) cell line | + |
| Promyelomonocytic (HL-60) cell line | − |
| T cell leukemia (Molt-4) cell line | ++ |
| T cell leukemia (Jurkat) cell line | ++ |

The results shown in Table 1 demonstrate that CD84Hy1 mRNA is expressed in cell lines derived from B cell lymphomas, multiple myelomas, T cell leukemias and myeloid leukemias.

EXAMPLE 2

CD84Hy1 mRNA is Highly Expressed in Primary B Cells, Lymph Node Tissue, Lymphomas and Leukemia Patient Tissues Expression of CD84Hy1 was determined in various healthy and tumor patient tissues (Table 2). Poly-A mRNA was isolated from the tonsilar lymph node, lymphoma, Hodgkin's disease, and acute myeloid leukemia (AML) tissue samples obtained from the Cooperative Human Tissue Network (CHTN, National Cancer Institute), whereas all other RNAs were purchased from Clontech (Palo Alto, Calif.) and Ambion (Austin, Tex.). All patient tissue samples from the CHTN were snap frozen immediately after surgical removal. Poly-A$^+$ mRNA was subjected to quantitative, real-time PCR analysis, as described in Example 1, to determine the relative expression of CD84Hy1 mRNA in the sample. All assays were performed in duplicate with the resulting values averaged and expressed as "−" for samples with no detectable CD84Hy1 mRNA in that sample to "+++" for samples with the highest mRNA copy number for CD84Hy1. The following quantitation scale for the real-time PCR experiments was used: "−"=0 copies/cell; "+"=approximately 1-10 copies/cell; "++"=approximately 11-50 copies/cell; and "+++"=approximately >50 copies/cell. The results are indicated in Table 2.

Tonsilar lymph nodes were used as non-lymphoma containing nodal tissue (7117), whereas 5348, 5856 and 6796 were B-cell follicular lymphomas and samples 6879 and 22601 were diffuse large B-cell lymphoma samples. One lymph node diagnosed with Hodgkin's disease and one splenic AML sample were also analyzed (566 and 565, respectively). The results in Table 1 (Example 1) and Table 2 demonstrate high levels of expression of CD84Hy1 in the B cell lymphoma cell lines CA-46, RL, HT, ST486 and GA-10 Additionally, peripheral blood B cells (CD-19+ cells), lymph node tissue and the multiple myeloma cell line U266 were also found to have high levels of expression. An intermediate level of expression of CD84Hy1 was found in the T cell leukemia lines Molt-4 and Jurkat, whereas healthy peripheral blood T cells (isolated with a pan T cell marker) were found to have only low levels of expression. Healthy peripheral blood monocytes (CD-14+) showed no detectable CD84Hy1, whereas the acute myeloid leukemia cell line, KG-1, and the AML patient tissue sample showed low levels of expression. Most non-hematopoeitic healthy tissues did not demonstrate expression of CD84Hy1 with the exception of lung, bladder, and cervix (low expression) and colon (with moderate levels of expression). Expression in these healthy tissues, in general, was found to be very low and may be accounted for by lymphoid tissues or leukocytes associated with the original collected tissue. Expression of CD84Hy1 in these tumor tissues demonstrates its usefulness as an immunotherapeutic target. Additionally, these results indicate that CD84Hy1 mRNA expression may be used as a diagnostic marker for certain cell types or disorders (e.g., B-cell lymphomas, AML, Hodgkin's disease and T cell lymphomas).

TABLE 2

| Patient Tissue | CD84Hy1 mRNA Expression |
| --- | --- |
| Tonsilar lymph node 7117 | ++ |
| Follicullar Lymphoma 5348 | ++ |
| Follicullar Lymphoma 5856 | +++ |
| Diffuse Large B Cell Lymphoma 6879 | ++ |
| Diffuse Large B Cell Lymphoma 22601 | +++ |
| Follicullar Lymphoma 6796 | +++ |
| T cell lymphoma 5664 | +++ |
| Hodgkin's Disease 566 | ++ |
| Acute Myeloid Leukemia 565 | + |
| Peripheral Blood B cells | +++ |
| Peripheral Blood Monocytes | − |
| Peripheral Blood T cells | + |
| Heart tissue | − |
| Ovary tissue | − |
| Placenta tissue | − |
| Brain tissue | − |
| liver tissue | − |
| lung tissue | + |
| adrenal tissue | − |
| Prostate tissue | − |
| spleen tissue | + |
| Testis tissue | − |
| bladder tissue | + |
| Colon tissue | ++ |
| Kidney tissue | − |
| Cervix tissue | + |
| Skeletal muscle tissue | − |
| Lymph node tissue | +++ |

EXAMPLE 3

Diagnostic Methods Using CD84Hy1-specific Antibodies to Detect CD84Hy1 Expression Expression of CD84Hy1 in tissue samples (normal or diseased) was detected using anti-CD84Hy1 antibodies (see Table 3). Samples were prepared for immunohistochemical (IHC) analysis (Clinomics Biosciences, Inc., Pittsfield, Mass.) by fixing tissues in 10% formalin embedding in paraffin, and sectioning using standard techniques. Sections were stained using the CD84Hy1-specific antibody followed by incubation with a secondary horse radish peroxidase (HRP)-conjugated antibody and visualized by the product of the HRP enzymatic reaction. Data as seen in Table 3 shows that CD84Hy1 is highly expressed on cell surface of hematopoietic tumor tissues. No expression of CD84Hy1 was observed on the cell surface of normal tissues.

TABLE 3

| Tissue | Positive | Total |
| --- | --- | --- |
| Acute myelogenous leukemia | 17 | 23 |
| Acute myelomonocytic leukemia | 11 | 11 |
| Acute lymphoblastic leukemia | 4 | 4 |
| Chronic myelogenous leukemia | 10 | 13 |
| Chronic lymphocytic leukemia | 10 | 15 |
| B cell large cell lymphoma | 6 | 7 |
| Malignant lymphoma | 5 | 8 |
| Acute leukemia | 1 | 2 |
| Lymphosarcoma cell leukemia | 2 | 2 |
| Normal prostate | 0 | 4 |
| Normal breast | 0 | 4 |
| Normal colon | 0 | 4 |
| Normal thyroid | 0 | 4 |
| Normal adrenal gland | 0 | 4 |
| Normal placenta | 0 | 4 |
| Normal tonsil | 0 | 4 |
| Normal lymph node | 0 | 4 |
| Normal spleen | 0 | 4 |
| Normal heart | 0 | 4 |
| Normal skeletal muscle | 0 | 4 |
| Normal liver | 0 | 4 |
| Normal pancreas | 0 | 4 |
| Normal ovary | 0 | 4 |
| Normal myometrium | 0 | 4 |
| Normal endometrium | 0 | 4 |
| Normal endocervical | 0 | 4 |
| Normal kidney | 0 | 4 |
| Normla seminal vesicle | 0 | 4 |
| Normal testis | 0 | 4 |
| Normal brain | 0 | 4 |
| Normal lung | 0 | 4 |
| Normal cerebellum | 0 | 4 |
| Normal cerebrum | 0 | 4 |

IHC analysis was also performed on tissues derived from autoimmune disorders. Table 4 shows that CD84Hy1 was overexpressed in tissues from systemic lupus erythematosus, Hasimoto thyroiditis, Sjörgen's syndrome, and pericarditis lupus, whereas normal tissue was negative for CD84Hy1 expression. Therefore, targeting CD84Hy1 may be useful in treating these and other autoimmune disorders.

TABLE 4

| Tissue | Positive | Total |
| --- | --- | --- |
| Systemic lupus erythematosus | 18 | 20 |
| Hasimoto Thyroiditis | 15 | 15 |
| Sjörgen's syndrome | 5 | 5 |
| Pericarditis lupus | 15 | 17 |

IHC analysis was performed on tissues derived from rejected organ transplants. Table 5 shows that CD84Hy1 was overexpressed in rejected heart, liver and kidney, whereas CD84Hy1 was not present on healthy tissues. Therefore, targeting CD84Hy1 may be useful to prevent or reduce tissue rejection after transplantation.

TABLE 5

| Tissue | Positive | Total |
| --- | --- | --- |
| Heart, transplant rejection | 21 | 27 |
| Liver, transplant rejection | 26 | 35 |
| Kidney, transplant rejection | 16 | 18 |
| Normal heart | 0 | 4 |
| Normal liver | 0 | 4 |
| Normal kidney | 0 | 4 |

Expression of CD84Hy1 on the surface of cells within a blood sample is detected by flow cytometry. Peripheral blood mononuclear cells (PBMC) are isolated from a blood sample using standard techniques. The cells are washed with ice-cold PBS and incubated on ice with the CD84Hy1-specific polyclonal antibody for 30 min. The cells are gently pelleted, washed with PBS, and incubated with a fluorescent anti-rabbit antibody for 30 min. on ice. After the incubation, the cells are gently pelleted, washed with ice cold PBS, and resuspended in PBS containing 0.1% sodium azide and stored on ice until analysis. Samples are analyzed using a FACScalibur flow cytometer (Becton Dickinson) and CELLQuest software (Becton Dickinson). Instrument setting are determined using FACS-Brite calibration beads (Becton-Dickinson).

Tumors expressing CD84Hy1 is imaged using CD84Hy1-specific antibodies conjugated to a radionuclide, such as $^{123}$I, and injected into the patient for targeting to the tumor followed by X-ray or magnetic resonance imaging.

EXAMPLE 4

Production of CD84Hy1-specific Antibodies

Cells expressing CD84Hy1 are identified using antibodies to CD84Hy1. Polyclonal antibodies are produced by DNA vaccination or by injection of peptide antigens into rabbits or other hosts. An animal, such as a rabbit, is immunized with a peptide from the extracellular region of CD84Hy1 conjugated to a carrier protein, such as BSA (bovine serum albumin) or KLH (keyhole limpet hemocyanin). The rabbit is initially immunized with conjugated peptide in complete Freund's adjuvant, followed by a booster shot every two weeks with injections of conjugated peptide in incomplete Freund's adjuvant. Anti-CD84Hy1 antibody is affinity purified from rabbit serum using CD84Hy1 peptide coupled to Affi-Gel 10 (Bio-Rad), and stored in phosphate-buffered saline with 0.1% sodium azide. To determine that the polyclonal antibodies are CD84Hy1-specific, an expression vector encoding CD84Hy1 is introduced into mammalian cells. Western blot analysis of protein extracts of non-transfected cells and the CD84Hy1-containing cells is performed using the polyclonal antibody sample as the primary antibody and a horseradish peroxidase-labeled anti-rabbit antibody as the secondary antibody. Detection of an approximately 60 kD band in the CD84Hy1-containing cells and lack thereof in the control cells indicates that the polyclonal antibodies are specific for CD84Hy1.

Monoclonal antibodies are produced by injecting mice with a CD84Hy1 peptide, with or without adjuvant. Subsequently, the mouse is boosted every 2 weeks until an appropriate immune response has been identified (typically 1-6 months), at which point the spleen is removed. The spleen is minced to release splenocytes, which are fused (in the presence of polyethylene glycol) with murine myeloma cells. The resulting cells (hybridomas) are grown in culture and selected for antibody production by clonal selection. The antibodies are secreted into the culture supernatant, facilitating the screening process, such as screening by an enzyme-linked immunosorbent assay (ELISA). Alternatively, humanized monoclonal antibodies are produced either by engineering a chimeric murine/human monoclonal antibody in which the murine-specific antibody regions are replaced by the human counterparts and produced in mammalian cells, or by using transgenic "knock out" mice in which the native antibody genes have been replaced by human antibody genes and immunizing the transgenic mice as described above.

EXAMPLE 5

In Vitro Antibody-dependent Cytotoxicity Assay

The ability of a CD84Hy1-specific antibody to induce antibody-dependent cell-mediated cytoxicity (ADCC) is determined in vitro. ADCC is performed using the CytoTox 96 Non-Radioactive Cytoxicity Assay (Promega; Madison, Wis.) (Homick et al., *Blood* 89: 4437-4447, (1997)) as well as effector and target cells. Peripheral blood mononuclear cells (PBMC) or neutrophilic polymorphonuclear leukocytes (PMN) are two examples of effector cells that can be used in this assay. PBMC are isolated from healthy human donors by Ficoll-Paque gradient centrifugation, and PMN are purified by centrifugation through a discontinuous percoll gradient (70% and 62%) followed by hypotonic lysis to remove residual erythrocytes. RA1 B cell lymphoma cells (for example) are used as target cells.

RA1 cells are suspended in RPMI 1640 medium supplemented with 2% fetal bovine serum and plated in 96-well V-bottom microtiter plates at $2\times10^4$ cells/well. CD84Hy1-specific antibody is added in triplicate to individual wells at 1 μg/ml, and effector cells are added at various effector:target cell ratios (12.5:1 to 50:1). The plates are incubated for 4 hours at 37° C. The supernatants are then harvested, lactate dehydrogenase release determined, and percent specific lysis calculated using the manufacture's protocols.

EXAMPLE 6

Toxin-conjugated CD84Hy1-specific Antibodies

Antibodies to CD84Hy1 are conjugated to toxins and the effect of such conjugates in animal models of cancer is evaluated. Chemotherapeutic agents, such as calicheamycin and carboplatin, or toxic peptides, such as ricin toxin, are used in this approach. Antibody-toxin conjugates are used to target cytotoxic agents specifically to cells bearing the antigen. The antibody-toxin binds to these antigen-bearing cells, becomes internalized by receptor-mediated endocytosis, and subsequently destroys the targeted cell. In this case, the antibody-toxin conjugate targets CD84Hy1-expressing cells, such as B cell lymphomas, and deliver the cytotoxic agent to the tumor resulting in the death of the tumor cells.

One such example of a toxin that may be conjugated to an antibody is carboplatin. The mechanism by which this toxin is conjugated to antibodies is described in Ota et al., *Asia-Oceania J. Obstet. Gynaecol.* 19: 449-457 (1993). The cytotoxicity of carboplatin-conjugated CD84Hy1-specific antibodies is evaluated in vitro, for example, by incubating CD84Hy1-expressing target cells (such as the RA1 B cell lymphoma cell line) with various concentrations of conjugated antibody, medium alone, carboplatin alone, or antibody alone. The antibody-toxin conjugate specifically targets and kills cells bearing the CD84Hy1 antigen, whereas, cells not bearing the antigen, or cells treated with medium alone, carboplatin alone, or antibody alone, show no cytotoxicity.

The antitumor efficacy of carboplatin-conjugated CD84Hy1-specific antibodies is demonstrated in in vivo murine tumor models. Five to six week old, athymic nude mice are engrafted with tumors subcutaneously or through intravenous injection. Mice are treated with the CD84Hy1-carboplatin conjugate or with a non-specific antibody-carboplatin conjugate. Tumor xenografts in the mouse bearing the CD84Hy1 antigen are targeted and bound to by the CD84Hy1-carboplatin conjugate. This results in tumor cell killing as evidenced by tumor necrosis, tumor shrinkage, and increased survival of the treated mice.

EXAMPLE 7

Radio-immunotherapy Using CD84Hy1-specific Antibodies

Animal models are used to assess the effect of antibodies specific to CD84Hy1 in delivery of radionuclides in radio-immunotherapy to treat lymphoma, hematological malignancies, and solid tumors. Human tumors are propagated in 5-6 week old athymic nude mice by injecting a carcinoma cell line or tumor cells subcutaneously. Tumor-bearing animals are injected intravenously with radio-labeled anti-CD84Hy1 antibody (labeled with 30-40 µCi of $^{131}$I, for example) (Behr, et al., *Int. J. Cancer* 77:787-795 (1988)). Tumor size is measured before injection and on a regular basis (i.e. weekly) after injection and compared to tumors in mice that have not received treatment. Anti-tumor efficacy is calculated by correlating the calculated mean tumor doses and the extent of induced growth retardation. To check tumor and organ histology, animals are sacrificed by cervical dislocation and autopsied. Organs are fixed in 10% formalin, embedded in paraffin, and thin sectioned. The sections are stained with hematoxylin-eosin.

EXAMPLE 8

Immunotherapy Using CD84Hy1-specific Antibodies

Animal models are used to evaluate the effect of CD84Hy1-specific antibodies as antibody-based immunotherapy. Human myeloma cells are injected into the tail vein of 5-6 week old nude mice whose natural killer cells have been eradicated. To evaluate the ability of CD84Hy1-specific antibodies in preventing tumor growth, mice receive an intraperitoneal injection with CD84Hy1-specific antibodies either 1 or 15 days after tumor inoculation followed by either a daily dose of 20 µg or 100 µg once or twice a week, respectively (Ozaki, et al., *Blood* 90:3179-3186 (1997)). Levels of human IgG (from the immune reaction caused by the human tumor cells) are measured in the murine sera by ELISA.

The effect of CD84Hy1-specific antibodies on the proliferation of myeloma cells is examined in vitro using a $^3$H-thymidine incorporation assay (Ozaki et al., supra). Cells are cultured in 96-well plates at $1\times10^5$ cells/ml in 100 µl/well and incubated with various amounts of CD84Hy1 antibody or control IgG (up to 100 µg/ml) for 24 h. Cells are incubated with 0.5 µCi $^3$H-thymidine (New England Nuclear, Boston, Mass.) for 18 h and harvested onto glass filters using an automatic cell harvester (Packard, Meriden, Conn.). The incorporated radioactivity is measured using a liquid scintillation counter.

The cytotoxicity of the CD84Hy1 monoclonal antibody is examined by the effect of complements on myeloma cells using a $^{51}$Cr-release assay (Ozaki et al., supra). Myeloma cells are labeled with 0.1 mCi $^{51}$Cr-sodium chromate at 37° C. for 1 h. $^{51}$Cr-labeled cells are incubated with various concentrations of CD84Hy1 monoclonal antibody or control IgG on ice for 30 min. Unbound antibody is removed by washing with medium. Cells are distributed into 96-well plates and incubated with serial dilutions of baby rabbit complement at 37° C. for 2 h. The supernatants are harvested from each well and the amount of $^{51}$Cr released is measured using a gamma counter. Spontaneous release of $^{51}$Cr is measured by incubating cells with medium alone, whereas maximum $^{51}$Cr release is measured by treating cells with 1% NP-40 to disrupt the plasma membrane. Percent cytotoxicity is measured by dividing the difference of experimental and spontaneous $^{51}$Cr release by the difference of maximum and spontaneous $^{51}$Cr release.

Antibody-dependent cell-mediated cytotoxicity (ADCC) for the CD84Hy1 monoclonal antibody is measured using a standard 4 h $^{51}$Cr-release assay (Ozaki et al., supra). Splenic mononuclear cells from SCID mice are used as effector cells and cultured with or without recombinant interleukin-2 (for example) for 6 days. $^{51}$Cr-labeled target myeloma cells ($1\times10^4$ cells) are placed in 96-well plates with various concentrations of anti-CD84Hy1 monoclonal antibody or control IgG. Effector cells are added to the wells at various effector to target ratios (12.5:1 to 50:1). After 4 h, culture supernatants are removed and counted in a gamma counter. The percentage of cell lysis is determined as above.

EXAMPLE 9

CD84Hy1-specific Antibodies as Immunosuppressants

Animal models are used to assess the effect of CD84Hy1-specific antibodies on blocking signaling through the CD84Hy1 receptor to suppress autoimmune diseases, such as arthritis or other inflammatory conditions, or rejection of organ transplants. Immunosuppression is tested by injecting mice with horse red blood cells (HRBCs) and assaying for the levels of HRBC-specific antibodies (Yang, et al., *Int. Immunopharm.* 2:389-397 (2002)). Animals are divided into five groups, three of which are injected with anti-CD84Hy1 antibodies for 10 days, and 2 of which receive no treatment. Two of the experimental groups and one control group are injected with either Earle's balanced salt solution (EBSS) containing $5-10\times10^7$ HRBCs or EBSS alone. Anti-CD84Hy1 antibody treatment is continued for one group while the other groups receive no antibody treatment. After 6 days, all animals are bled by retro-orbital puncture, followed by cervical dislocation and spleen removal. Splenocyte suspensions are prepared and the serum is removed by centrifugation for analysis.

Immunosupression is measured by the number of B cells producing HRBC-specific antibodies. The Ig isotype (for example, IgM, IgG1, IgG2, etc.) is determined using the IsoDetect™ Isotyping kit (Stratagene, La Jolla, Calif.). Once the Ig isotype is known, murine antibodies against HRBCs are measured using an ELISA procedure. 96-well plates are coated with HRBCs and incubated with the anti-HRBC antibody-containing sera isolated from the animals. The plates are incubated with alkaline phosphatase-labeled secondary antibodies and color development is measured on a microplate reader (SPECTRAmax 250, Molecular Devices) at 405 nm using p-nitrophenyl phosphate as a substrate.

Lymphocyte proliferation is measured in response to the T and B cell activators concanavalin A and lipopolysaccharide, respectively (Jiang and Moller, *J. Immunol.* 154:3138-3146 (1995). Mice are randomly divided into 2 groups, 1 receiving anti-CD84Hy1 antibody therapy for 7 days and 1 as a control. At the end of the treatment, the animals are sacrificed by cervical dislocation, the spleens are removed, and splenocyte suspensions are prepared as above. For the ex vivo test, the same number of splenocytes are used, whereas for the in vivo test, the anti-CD84Hy1 antibody is added to the medium at the beginning of the experiment. Cell proliferation is also assayed using the $^3$H-thymidine incorporation assay described above (Ozaki, et al., *Blood* 90:3179-3186 (1997)).

EXAMPLE 10

Cytokine Secretion in Response to CD84Hy1 Peptide Fragments

Assays are carried out to assess activity of fragments of the CD84Hy1 protein, such as the Ig domain, to stimulate cytokine secretion and to stimulate immune responses in NK cells, B cells, T cells, and myeloid cells. Such immune responses can be used to stimulate the immune system to recognize and/or mediate tumor cell killing or suppression of growth. Similarly, this immune stimulation can be used to target bacterial or viral infections. Alternatively, fragments of the CD84Hy1 that block activation through the CD84Hy1 receptor may be used to block immune stimulation in natural killer (NK), B, T, and myeloid cells.

Fusion proteins containing fragments of the CD84Hy1, such as the Ig domain (CD84Hy1-Ig), are made by inserting a CD33 leader peptide, followed by a CD84Hy1 domain fused to the Fc region of human IgG1 into a mammalian expression vector, which is stably transfected into NS-1 cells, for example. The fusion proteins are secreted into the culture supernatant, which is harvested for use in cytokine assays, such as interferon-γ (IFN-γ) secretion assays (Martin, et al., *J. Immunol.* 167:3668-3676 (2001)).

PBMCs are activated with a suboptimal concentration of soluble CD3 and various concentrations of purified, soluble anti-CD84Hy1 monoclonal antibody or control IgG. For CD84Hy1-Ig cytokine assays, anti-human Fc Ig at 5 or 20 µg/ml is bound to 96-well plates and incubated overnight at 4° C. Excess antibody is removed and either CD84Hy1-Ig or control Ig is added at 20-50 µg/ml and incubated for 4 h at room temperature. The plate is washed to remove excess fusion protein before adding cells and anti-CD3 to various concentrations. Supernatants are collected after 48 h of culture and IFN-γ levels are measured by sandwich ELISA, using primary and biotinylated secondary anti-human IFN-γ antibodies as recommended by the manufacturer.

EXAMPLE 11

Tumor Imaging Using CD84Hy1-specific Antibodies

CD84Hy1-specific antibodies are used for imaging CD84Hy1-expressing cells in vivo. Six-week-old athymic nude mice are irradiated with 400 rads from a cesium source. Three days later the irradiated mice are inoculated with $4 \times 10^7$ RA1 cells and $4 \times 10^6$ human fetal lung fibroblast feeder cells subcutaneously in the thigh. When the tumors reach approximately 1 cm in diameter, the mice are injected intravenously with an inoculum containing 100 µCi/10 µg of $^{131}$I-labeled CD84Hy1-specific antibody. At 1, 3, and 5 days postinjection, the mice are anesthetized with a subcutaneous injection of 0.8 mg sodium pentobarbital. The immobilized mice are then imaged in a prone position with a Spectrum 91 camera equipped with a pinhole collimator (Raytheon Medical Systems; Melrose Park, Ill.) set to record 5,000 to 10,000 counts using the Nuclear MAX Plus image analysis software package (MEDX Inc.; Wood Dale, Ill.) (Homick, et al., *Blood* 89: 4437-4447 (1997)).

We claim:

1. A method of diagnosing a hematopoietic-based cancer comprising the steps of:
   a) detecting or measuring the expression of a CD84Hy1 protein comprising the amino acid sequence SEQ ID NO: 2 on a cell; and
   b) comparing said expression to a standard indicative of said disease.

2. A method of diagnosing a hematopoietic-based cancer comprising the steps of:
   a) detecting or measuring the expression of a CD84Hy1 protein comprising the amino acid sequence SEQ ID NO: 2 on a cell; and
   b) comparing said expression to normal tissue.

3. The method of claim 1 or 2, wherein the hematopoietic-based cancer is selected from the group consisting of acute myelogenous leukemia, acute myelomonocytic leukemia, acute lymphoblastic leukemia, chronic lymphocytic leukemia, B cell large cell lymphoma, malignant lymphoma, lymphosarcoma cell leukemia, B-cell lymphoma, T-cell lymphoma, acute myeloid leukemia, and Hodgkin's Disease.

4. The method of claim 1 or 2, wherein the protein expression is detected or measured using anti-CD84Hy1 antibodies.

* * * * *

SEQUENCE LISTING

```
<160> NUMBER OF SEQ ID NOS: 2

<210> SEQ ID NO 1
<211> LENGTH: 996
<212> TYPE: DNA
<213> ORGANISM: Homo sapiens
<220> FEATURE:
<221> NAME/KEY: CDS
<222> LOCATION: (1)..(996)
<223> OTHER INFORMATION:

<400> SEQUENCE: 1 atg ttg tgg ctg ttc caa tcg ctc ctg ttt gtc ttc tgc ttt ggc cca      48
Met Leu Trp Leu Phe Gln Ser Leu Leu Phe Val Phe Cys Phe Gly Pro
1               5                   10                  15 ggg aat gta gtt tca caa agc agc tta acc cca ttg atg gtg aac ggg      96
Gly Asn Val Val Ser Gln Ser Ser Leu Thr Pro Leu Met Val Asn Gly
            20                  25                  30 att ctg ggg gag tca gta act ctt ccc ctg gag ttt cct gca gga gag     144
Ile Leu Gly Glu Ser Val Thr Leu Pro Leu Glu Phe Pro Ala Gly Glu
```

```
                35                  40                  45
aag gtc aac ttc atc act tgg ctt ttc aat gaa aca tct ctt gcc ttc      192
Lys Val Asn Phe Ile Thr Trp Leu Phe Asn Glu Thr Ser Leu Ala Phe
     50                  55                  60 ata gta ccc cat gaa acc aaa agt cca gaa atc cac gtg act aat ccg      240
Ile Val Pro His Glu Thr Lys Ser Pro Glu Ile His Val Thr Asn Pro
 65                  70                  75                  80 aaa cag gga aag cga ctg aac ttc aca cag tcc tac tcc ttg caa ctc      288
Lys Gln Gly Lys Arg Leu Asn Phe Thr Gln Ser Tyr Ser Leu Gln Leu
                 85                  90                  95 agc aac ctg aag ata gaa gac aca ggc tct tac aga gcc cag ata tcc      336
Ser Asn Leu Lys Ile Glu Asp Thr Gly Ser Tyr Arg Ala Gln Ile Ser
            100                 105                 110 aca aag acc tct gca aag ctg tcc agt tac act ctg agg ata tta aga      384
Thr Lys Thr Ser Ala Lys Leu Ser Ser Tyr Thr Leu Arg Ile Leu Arg
        115                 120                 125 caa ctg agg aac ata caa gtt acc aat cac agt cag cta ttt cag aat      432
Gln Leu Arg Asn Ile Gln Val Thr Asn His Ser Gln Leu Phe Gln Asn
    130                 135                 140 atg acc tgt gag ctc cat ctg act tgc tct gtg gag gat gca gat gac      480
Met Thr Cys Glu Leu His Leu Thr Cys Ser Val Glu Asp Ala Asp Asp
145                 150                 155                 160 aat gtc tca ttc aga tgg gag gcc ttg gga aac aca ctt tca agt cag      528
Asn Val Ser Phe Arg Trp Glu Ala Leu Gly Asn Thr Leu Ser Ser Gln
                165                 170                 175 cca aac ctc act gtc tcc tgg gac ccc agg att tcc agt gaa cag gac      576
Pro Asn Leu Thr Val Ser Trp Asp Pro Arg Ile Ser Ser Glu Gln Asp
            180                 185                 190 tac acc tgc ata gca gag aat gct gtc agt aat tta tcc ttc tct gtc      624
Tyr Thr Cys Ile Ala Glu Asn Ala Val Ser Asn Leu Ser Phe Ser Val
        195                 200                 205 tct gcc cag aag ctt tgc gaa gat gtt aaa att caa tat aca gat acc      672
Ser Ala Gln Lys Leu Cys Glu Asp Val Lys Ile Gln Tyr Thr Asp Thr
    210                 215                 220 aaa atg att ctg ttt atg gtt tct ggg ata tgc ata gtc ttc ggt ttc      720
Lys Met Ile Leu Phe Met Val Ser Gly Ile Cys Ile Val Phe Gly Phe
225                 230                 235                 240 atc ata ctg ctg tta ctt gtt ttg agg aaa aga aga gat tcc cta tct      768
Ile Ile Leu Leu Leu Leu Val Leu Arg Lys Arg Arg Asp Ser Leu Ser
                245                 250                 255 ttg tct act cag cga aca cag ggc ccc gag tcc gca agg aac cta gag      816
Leu Ser Thr Gln Arg Thr Gln Gly Pro Glu Ser Ala Arg Asn Leu Glu
            260                 265                 270 tat gtt tca gtg tct cca acg aac aac act gtg tat gct tca gtc act      864
Tyr Val Ser Val Ser Pro Thr Asn Asn Thr Val Tyr Ala Ser Val Thr
        275                 280                 285 cat tca aac agg gaa aca gaa atc tgg aca cct aga gaa aat gat act      912
His Ser Asn Arg Glu Thr Glu Ile Trp Thr Pro Arg Glu Asn Asp Thr
    290                 295                 300 atc aca att tac tcc aca att aat cat tcc aaa gag agt aaa ccc act      960
Ile Thr Ile Tyr Ser Thr Ile Asn His Ser Lys Glu Ser Lys Pro Thr
305                 310                 315                 320 tct tcc agg gca act gcc ctt gac aat gtc gtg taa                       996
Ser Ser Arg Ala Thr Ala Leu Asp Asn Val Val
                325                 330

<210> SEQ ID NO 2
<211> LENGTH: 331
<212> TYPE: PRT
<213> ORGANISM: Homo sapiens
```

```
<400> SEQUENCE: 2

Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
                20                  25                  30

Ile Leu Gly Glu Ser Val Thr Leu Pro Leu Glu Phe Pro Ala Gly Glu
                35                  40                  45

Lys Val Asn Phe Ile Thr Trp Leu Phe Asn Glu Thr Ser Leu Ala Phe
                50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Ile Glu Asp Thr Gly Ser Tyr Arg Ala Gln Ile Ser
                100                 105                 110

Thr Lys Thr Ser Ala Lys Leu Ser Ser Tyr Thr Leu Arg Ile Leu Arg
                115                 120                 125

Gln Leu Arg Asn Ile Gln Val Thr Asn His Ser Gln Leu Phe Gln Asn
        130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
                180                 185                 190

Tyr Thr Cys Ile Ala Glu Asn Ala Val Ser Asn Leu Ser Phe Ser Val
                195                 200                 205

Ser Ala Gln Lys Leu Cys Glu Asp Val Lys Ile Gln Tyr Thr Asp Thr
210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Glu Ser Ala Arg Asn Leu Glu
                260                 265                 270

Tyr Val Ser Val Ser Pro Thr Asn Asn Thr Val Tyr Ala Ser Val Thr
                275                 280                 285

His Ser Asn Arg Glu Thr Glu Ile Trp Thr Pro Arg Glu Asn Asp Thr
                290                 295                 300

Ile Thr Ile Tyr Ser Thr Ile Asn His Ser Lys Glu Ser Lys Pro Thr
305                 310                 315                 320

Ser Ser Arg Ala Thr Ala Leu Asp Asn Val Val
                325                 330
```